US008980607B2

(12) United States Patent
Ochiai

(10) Patent No.: US 8,980,607 B2
(45) Date of Patent: Mar. 17, 2015

(54) GLYCEROL-3-PHOSPHATE ACYL TRANSFERASE

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 38 days.

(21) Appl. No.: 13/496,081

(22) PCT Filed: Sep. 21, 2010

(86) PCT No.: PCT/JP2010/066280
§ 371 (c)(1),
(2), (4) Date: May 14, 2012

(87) PCT Pub. No.: WO2011/034199
PCT Pub. Date: Mar. 24, 2011

(65) Prior Publication Data
US 2013/0252308 A1 Sep. 26, 2013

(30) Foreign Application Priority Data
Sep. 18, 2009 (JP) .................................. 2009-217646

(51) Int. Cl.
| | | |
|---|---|---|
| C12N 9/20 | (2006.01) | |
| C12N 1/20 | (2006.01) | |
| C12N 15/00 | (2006.01) | |
| C07H 21/04 | (2006.01) | |
| C12N 9/10 | (2006.01) | |
| A23L 1/28 | (2006.01) | |
| A23L 1/30 | (2006.01) | |
| C12P 7/64 | (2006.01) | |
| A61K 8/36 | (2006.01) | |
| A61Q 19/00 | (2006.01) | |
| A61K 8/99 | (2006.01) | |
| A23D 7/00 | (2006.01) | |
| A23D 9/00 | (2006.01) | |
| C11B 1/00 | (2006.01) | |

(52) U.S. Cl.
CPC .................. *C12N 9/1029* (2013.01); *A23L 1/28* (2013.01); *A23L 1/3006* (2013.01); *C12P 7/6409* (2013.01); *C12P 7/6463* (2013.01); *C12Y 203/01015* (2013.01); *A61K 8/361* (2013.01); *A61Q 19/00* (2013.01); *A61K 8/99* (2013.01); *A23D 7/00* (2013.01); *A23D 9/00* (2013.01); *C11B 1/00* (2013.01)
USPC ..................... 435/193; 435/252.3; 435/320.1; 536/23.2

(58) Field of Classification Search
CPC .. C12N 9/1029; C12N 15/815; C12N 9/0083; C12N 15/52; C12N 15/746; C12N 1/16; C12N 9/0006; C12N 9/0071; C12N 9/90; C12N 15/8247
USPC ....................... 435/193, 252.3, 131
See application file for complete search history.

(56) References Cited

U.S. PATENT DOCUMENTS

| | | |
|---|---|---|
| 8,110,388 B2 | 2/2012 | Ochiai et al. |
| 2005/0287652 A1 | 12/2005 | Damude et al. |
| 2006/0094091 A1 | 5/2006 | Macool et al. |
| 2006/0094092 A1 | 5/2006 | Damude et al. |
| 2006/0174376 A1 | 8/2006 | Renz et al. |
| 2010/0159110 A1 | 6/2010 | Ochiai et al. |
| 2012/0115231 A1 | 5/2012 | Ochiai |

FOREIGN PATENT DOCUMENTS

| | | |
|---|---|---|
| EP | 2 157 179 A1 | 2/2010 |
| JP | 2001-245687 | 9/2001 |
| JP | 2008-518627 A | 6/2008 |
| WO | 2004/087902 A2 | 10/2004 |
| WO | 2008/156026 A1 | 12/2008 |

OTHER PUBLICATIONS

Ngo et al. In the Protein Folding Problem and Tertiary Structure Prediction. Merz et al. (ed.), Birkhauser, Boston, MA, pp. 433 and 492-495, 1994.*
Witkowski et al., Conversion of a β-Ketoacyl Synthase to a Malonyl Decarboxylase by Replacement of the Active-Site Cysteine with Glutamine. Biochemistry 38:11643-11650, 1999.*
Seffernick et al., Melamine Deaminase and Atrazine Chlorohydrolase: 98 Percent Identical but Functionally Different. J. Bacteriol. 183(8):2405-2410, 2001.*
Calder, "n-3 Fatty Acids, Inflammation, and Immunity—Relevance to Postsurgical and Critically Ill Patients" *Lipids*, vol. 39, No. 12, pp. 1147-1161 (2004).
Dircks et al., "Mammalian Mitochondrial Glycerol-3-Phosphate Acyltransferase" *Biochimica et Biophysica Acta*, vol. 1348, pp. 17-26 (1997).
Murata et al., "Glycerol-3-Phosphate Acyltransferase in Plants" *Biochimica et Biophysica Acta*, vol. 1348, pp. 10-16 (1997).
Zheng et al., "The Initial Step of the Glycerolipid Pathway" *The Journal of Biological Chemistry*, vol. 276, No. 45, pp. 41710-41716 (2001).
Mishra et al., "Purification and Characterization of Thiol-Reagent-Sensitive Glycerol-3-Phosphate Acyltransferase from the Membrane Fraction of an Oleaginous Fungus" *Biochem. J.*, vol. 355, pp. 315-322 (2001).
Chatrattanakunchai et al., "Oil Biosynthesis in Microsomal Membrane Preparations from *Mortierella alpina*" *Biochemical Society Transactions*, vol. 28, No. 6., pp. 707-709 (2000).

(Continued)

*Primary Examiner* — Tekchand Saidha
(74) *Attorney, Agent, or Firm* — Greenblum & Bernstein, P.L.C.

(57) ABSTRACT

The present invention relates to glycerol-3-phosphate acyltransferases and polynucleotides encoding the same. The present invention provides non-naturally occurring polynucleotides encoding a protein having at least 85% homology to the amino acid sequence of SEQ ID NO: 2, as well as an expression vector and transformant comprising such polynucleotides. The present invention also provides a method for producing food using the transformant, and food produced by the method.

16 Claims, 7 Drawing Sheets

(56) References Cited

OTHER PUBLICATIONS

Kamisaka et al., "Purification and Characterization of Diacylglycerol Acyltransferase from Lipid Body Fraction of an Oleaginous Fungus", *J. Biochem.*, vol. 121, No. 6, pp. 1107-1114 (1997).

U.S. Appl. No. 13/512,109 to Misa Ochiai, filed May 25, 2012.

International Search Report issued with respect to PCT/JP2010/066280, mail date is Nov. 2, 2010.

Extended European Search Report for European Patent Application No. 10817312.1, mailed Mar. 13, 2013.

Huang et al., "Cloning of Δ12- and Δ6-Desaturases from *Mortierella alpina* and Recombinant Production of γ-Linolenic Acid in *Saccharomyces cerevisiae*" Lipids, vol. 34, No. 7, pp. 649-659, 1999.

Japanese Office Action for JP App. No. 2011-531994, mailed Oct. 16, 2012, along with an English language translation.

* cited by examiner

FIG. 1-1

```
           1                                                                                                    100
genome     ATGGGTCTCCAGATCTATGACTTCGTCTCATTCTTCTTCACCCTCCTGCTGGACATCTTCTTCAGGGAAATCCGTCCTCGGGGGGCCCACAAGATCCCCC
CDS        ATGGGTCTCCAGATCTATGACTTCGTCTCATTCTTCTTCACCCTCCTGCTGGACATCTTCTTCAGGGAAATCCGTCCTCGGGGGGCCCACAAGATCCCCC 101                                                                                                  200
genome     GACAAGGACCCGTCATTTTTGTCGGCGCCCCTCATGCCAATCAGGTAGGCCATTGTCTTTAATTTGGAAGCTTAAAGTCACCACTTTATGCGCAAGAGCC
CDS        GACAAGGACCCGTCATTTTTGTCGGCGCCCCGTCATGCCAATCAG---------------------------------------------------

201                                                                                                  300
genome     TCATGGTCCGTAAGGTACTAATCGCTGCTTGCATGAAACTAGTTTGTTGATCCACTCGTGTTGATGCGCGAATGTGGCCGACGAGTCTCGTTCCTGGCTG
CDS        ----------------------------------------TTTGTTGATCCACTCGTGTTGATGCGCGAATGTGGCCGACGAGTCTCGTTCCTGGCTG 301                                                                                                  400
genome     CCAAAAAGTCAATGGACCGTCGCTGGATAGGCGCCATGGGCGCGTTCCATGAATGCCAGTAAGTACAAAAAAAAAAAAAAAAAAAAAAAAAAAAACGACCTAT
CDS        CCAAAAAGTCAATGGACCGTCGCTGGATAGGCGCCATGGGCGCGTTCCATGAATGCCA---------------------------------------

401                                                                                                  500
genome     TCGGCGTGAGAGTGGCAACGAAGGGGAGAGAGATACACAAACGGGCCTTTTGAGTGCGTGTGTGCGTGGGAAAAGAATACGAGAACATTCTCTTGCCAGC
CDS        ----------------------------------------------------------------------------------------------------

501                                                                                                  600
genome     AAAACGCGCTTCCTTTCTCTTTTCTCCGACGTTGTTGATGGCGCCTTTTGTATACACTTCCTATCCATCGTCCCTATCCGAGAGATCAAGGTTTTCTGCG
CDS        ----------------------------------------------------------------------------------------------------

601                                                                                                  700
genome     TCGTGTTATTTTAGGCCACTCCGCCGAGATAACAGACACGAGCTACTGACCGATTCAACGAGGGTTCACACACCGTCCACAACCACCTGAGAAATGTGCA
CDS        ----------------------------------------------------------------------------------------------------

701                                                                                                  800
genome     GGCCATGACGAGTGTCGTGTGCCGTTTCTTCTTTGATACCATACCGCTCCTGCAGTCATGGGCCATCCGTTATGCCCTGACCTCAGCATTGGAATCTGAC
CDS        ----------------------------------------------------------------------------------------------------

801                                                                                                  900
genome     GTTTTTTTCTGCTGGCTCTCTTGTCATCTGCGTTAGTTCGTGTGGAGCGTCCTGAGGACTTGGCTAAGGCTGGTTCGGGAACGATCAAACTGGTGGATCG
CDS        ------------------------------------TTCCTGTGGAGCGTCCTGAGGACTTGGCTAAGGCTGGTTCGGGAACGATCAAACTGGTGGATCG 901                                                                                                 1000
genome     CTATGGCGACCCTCTCCGCATCACTGGGCTCGGTACCAAATTCACAAAGGAACTCTTTGTCGGCGACCAGATTTCGCTCCCAAAGGACGTTGGAACCTCG
CDS        CTATGGCGACCCTCTCCGCATCACTGGGCTCGGTACCAAATTCACAAAGGAACTCTTTGTCGGCGACCAGATTTCGCTCCCAAAGGACGTTGGAACCTCG 1001                                                                                                1100
genome     GCTGTGGTCGAGATCATCTCGGACACTGAACTGATTGTCAAGAAAGAGTTCAAGGAGCTCAAGGCACTGGAGCTTTTAACCAGTGCTGAGGGATCCAAGT
CDS        GCTGTGGTCGAGATCATCTCGGACACTGAACTGATTGTCAAGAAAGAGTTCAAGGAGCTCAAGGCACTGGAGCTTTTAACCAGTGCTGAGGGATCCAAGT 1101                                                                                                1200
genome     ACAAGTGCATGCCTCACATGGACCAGAGCAAGGTCTACAAGACTGTTTTTGAACGCTTAAATGCTGGCCATTGTGTTGGCATCTTTCCTGAAGGAGGTTC
CDS        ACAAGTGCATGCCTCACATGGACCAGAGCAAGGTCTACAAGACTGTTTTTGAACGCTTAAATGCTGGCCATTGTGTTGGCATCTTTCCTGAAGGAGGTTC 1201                                                                                                1300
genome     ACACGATCGTGCAGAGATGCTGCCCCTGAAAGGTAAGCGCCCCTCGTGAGCATCCCAACATAACGGGAATTACCCCACACTTGCCTTGTCCTTGCGCATC
CDS        ACACGATCGTGCAGAGATGCTGCCCCTGAAAG---------------------------------------------------

1301                                                                                                1400
genome     TCTGTATGAACGTACACTGATTGCATTGCATATCTCCGTTTGGATTGGATAGCTGGTGTCACCGATCATGGCGCTTGGCGGACTGGCGGCTAACCCTGACC
CDS        ------------------------------------CTGGTGTCACCGATCATGGCGCTTGGCGGACTGGCGGCTAACCCTGACC
```

FIG. 1-2

```
         1401                                                                                    1500
genome   TGGACCTTAAAATTGTGACCTGCGGCCTGAACTATTTCCACCCCCATCGATTCCGTTCTCGCGCCGTTGTTGAGTTTGGTGAGCCTTTGACCGTGCCTCC
CDS      TGGACCTTAAAATTGTGACCTGCGGCCTGAACTATTTCCACCCCCATCGATTCCGTTCTCGCGCCGTTGTTGAGTTTGGTGAGCCTTTGACCGTGCCTCC 1501                                                                                    1600
genome   AGAACTTGTCGAGATGTACAAGAGGGGTGGAGCTGAGAAGCGCGAGGCCTGCGGAAAGCTCCTCGACACCATCTACGATGCACTCAAGAATGTCACACTG
CDS      AGAACTTGTCGAGATGTACAAGAGGGGTGGAGCTGAGAAGCGCGAGGCCTGCGGAAAGCTCCTCGACACCATCTACGATGCACTCAAGAATGTCACACTG 1601                                                                                    1700
genome   AACGCCCCCGATTACGAAACACTCATGGTGAGGATTGGCGGTGTTTTTGCATGCGGCTTATGTCATTTGGAGCAATTGAGACCAACGTTAACTTAAAGGG
CDS      AACGCCCCCGATTACGAAACACTCATGGT---------------------------------------------------------------------

1701                                                                                    1800
genome   CTTTAATATGGCTGGACTGGATGTAGGTTATTCAAGCTGCCCGCCGTCTCTACAAGCCAACACATCGCAAGCTGCAGATCTCTCAAGTTGTGGAGTTGAA
CDS      -----------------------------------TATTCAAGCTGCCCGCCGTCTCTACAAGCCAACACATCGCAAGCTGCAGATCTCTCAAGTTGTGGAGTTGAA 1801                                                                                    1900
genome   CCGTCGCTTCGTCGCTGGTTATCTGCACTTTCAGGACAACCCAAAGGTGATTGATACAAAGGACAAAGTTATGCACTACAAGACTCAGCTACGCTATCAT
CDS      GCGTCGGTTCGTCGCTGGTTATCTGCACTTTCAGGACAACCCAAAGGTGATTGATACAAAGGACAAAGTTATGCACTACAACACTCAGCTACGCTATCAT 1901                                                                                    2000
genome   GGACTTCGCGACCACCAGGTCAACATCGGCACAACTCGGCGACATGCCATTGAACTATTGATTTGGCGAGTTGTGCAGATGGTCTTTTTTGAGTCTACTAG
CDS      GGACTTCGCGACCACCAGGTCAACATCGGCACAACTCGGCGACATGCCATTGAACTATTGATTTGGCGAGTTGTGCAGATGGTCTTTTTTGAGTCTACTAG 2001                                                                                    2100
genome   CGCTTCCAGGGTAAGAACGAATGCAGCAGTGGTGTCATGTGACAGACTTTTGTGTGGGCGGTTAGATTGAGGCTAGCACTACTTCACGCGATTGGATATT
CDS      CGCTTCCAGG------------------------------------------------------------------------------------------

2101                                                                                    2200
genome   AGACTAACGCTTTCTCTACTTTTAGTACCATGATGAATCTTCCAGTTGCCATCGTTGCTCGCATCATCAGCAACAAGAAGGCCAAGGGTATGTAATCGTC
CDS      ---------------------------------TACCATGATGAATCTTCCAGTTGCCATCGTTGCTCGCATCATCAGCAACAAGAAGGCCAAGG------

2201                                                                                    2300
genome   GCAATGACAGCGACAAATCTTTTGATTATCGGGAGAATGGCGTCAGAGGAAAAAGGCCAAGGCTAACGCTATAATCATTTTCACAATTTAACAGAGGCTT
CDS      ------------------------------------------------------------------------------------------AGGCTT 2301                                                                                    2400
genome   TGGCTGCATCGACCGTGAAAATTGCAGGAAGGGACGTTCTAGCCACATGGAAGTTGCTTGTGGCCCTGGGATTGATGCCCGTCCTTTACTTTTCGTACTC
CDS      TGGCTGCATCGACCGTGAAAATTGCAGGAAGGGACGTTCTAGCCACATGGAAGTTGCTTGTGGCCCTGGGATTGATGCCCGTCCTTTACTTTTCGTACTC 2401                                                                                    2500
genome   GTTTGTTATCTTTTTGCTGTGTGGACGGTTCGACATTACGCTCAAGACCCGCCTCCTGATCGCTTGGGCGGCTTGGGCCTGCATTCCGTTTGTGACCTAC
CDS      GTTTGTTATCTTTTTGCTGTGTGGACGGTTCGACATTACGCTCAAGACCCGCCTCCTGATCGCTTGGGCGGCTTGGGCCTGCATTCCGTTTGTGACCTAC 2501                                                                                    2600
genome   GCCAGTATCCGTTTCGGTGAGGTGGGTATCGATATCTTCAAGTCGATCCGTCCTCTCTTCTTGTCAATCATTCCCGGCGAGGAAAACACGATCAATGAGC
CDS      GCCAGTATCCGTTTCGGTGAGGTGGGTATCGATATCTTCAAGTCGATCCGTCCTCTCTTCTTGTCAATCATTCCCGGCGAGGAAAACACGATCAATGAGC 2601                                                                                    2700
genome   TCCGCAAGTCGCGTGCAGAGCTTCAAAAGACCATCAACGAGCTCATCAATGAGCTGGGCGCGGAAATATACCCCGACTTTGATTCCAAACGAATCTTGGA
CDS      TCCGCAAGTCGCGTGCAGAGCTTCAAAAGACCATCAACGAGCTCATCAATGAGCTGGGCGCGGAAATATACCCCGACTTTGATTCCAAACGAATCTTGGA 2701                                                                                    2800
genome   CCCTTCGCCAAACGATCGACCCAGCCGCGGGGCGTCGCGCTCCGCCTCGGGCACCAACCTTGCGCAGACCATTTTTCAACACCATGAACACGGCCACACAG
CDS      CCCTTCGCCAAACGATCGACCCAGCCGCGGGGCGTCGCGCTCCGCCTCGGGCACCAACCTTGCGCAGACCATTTTTCAACACCATGAACACGGCCACACAG
```

FIG. 1-3

```
         2801                                                                                                  2900
genome   CGGCTAAACCAATGGCTCGGTATGGATGGGCGCTTCGAGTCGGAGGACGGTGTGGAGGACGGATCGGATGCGACGACGTGTTCTTTTTCGTCAACCCTGCAGGAG
   CDS   CGGCTAAACCAATGGCTCGGTATGGATGGGCGCTTCGAGTCGGAGGACGGTGTGGAGGACGGATCGGATGCGACGACGTGTTCTTTTTCCTCAACCCTGAGGAG 2901                                                                                                  3000
genome   CGATCGAAGGGCGATCGAGGAGGAGTCTTCTTGGGGTGCTGGAGCATGGAGGCCTTCGTCTGCTGGAGGCGTTGTCGGTCTGGGTCAAGGAGTCGGAGTCG
   CDS   CGATCGAAGGGCGATCGAGGAGGAGTCTTCTTGGGGTGCTGGAGCATGGAGGCCTTCGTCTGCTGGAGGCGTTGTCGGTCTGGGTCAAGGAGTCGGAGTCG 3001                                                                                                  3100
genome   GACGAGCTGGTTTGGCGTCAGGGAGATTCAAGCTGGAGGCATTGACAGAGCTGCCAAAGGATAAGCCTTTTGGGGAGGTGACA
   CDS   GACGAGCTGGTTTGGCGTCAGGGAGATTCAAGCTGGAGGCATTGACAGAGCTGCCAAAGGATAAGCCTTTTGGGGAGGTGACA 3101                                                                                                  3200
genome   CGAGGACTCAGCTTGAGTCGGCAAGCAGAAGCATGGAGACTGGTGGGGAGGAGATTGAGAAGCAGGGGGATTTATGCATGAGG
   CDS   CGAGGACTCAGCTTGAGTCGGCAAGCAGAAGCATGGAGACTGGTGGGGAGGAGATTGAGAAGCAGGGGGATTTATGCATGAGG 3201              3280
genome   GACAGTTTGTCAGCACACCGGCCCATCACCGGTTCAGAACATGGATGATCCTATGGATGCAGTCAAGTCTAAGGAGGCATAA
   CDS   GACAGTTTGTCAGCACACCGGCCCATCACCGGTTCAGAACATGGATGATCCTATGGATGCAGTCAAGTCTAAGGAGGCATAA
```

FIG. 2-1

```
   1  ATGGGTCTCCAGATCTATGACTTCGTCTCATTCTTCTTCACCCTCCTGCTCGACATCTTCTTCAGGGAAATCCGTCCTCGGGGGGCCCAC
      M  G  L  Q  I  Y  D  F  V  S  F  F  F  T  L  L  L  D  I  F  F  R  E  I  R  P  R  G  A  H

91  AAGATCCCCCGACAAGGACCCGTCATTTTTGTCGCCGCCCCTCATGCCAATCAGTTTGTTGATCCACTCGTGTTGATGCGCGAATGTGGC
      K  I  P  R  Q  G  P  V  I  F  V  A  A  P  H  A  N  Q  F  V  D  P  L  V  L  M  R  E  C  G

181  CGACGAGTCTCGTTCCTGGCTGCCAAAAAGTCAATGGACCGTCGCTGGATAGGCGCCATGGCGCGTTCCATGAATGCCATTCCTGTGGAG
      R  R  V  S  F  L  A  A  K  K  S  M  D  R  R  W  I  G  A  M  A  R  S  M  N  A  I  P  V  E

271  CGTCCTCAGGACTTGGCTAAGGCTGGTTCGGGAACGATCAAACTGGTGGATCGCTATGGCGACCCTCTCCGCATCACTGGGCTCGGTACC
      R  P  Q  D  L  A  K  A  G  S  G  T  I  K  L  V  D  R  Y  G  D  P  L  R  I  T  G  L  G  T

361  AAATTCACAAAGGAACTCTTTGTCGGCGACCAGATTTCGCTCCCAAAGGACGTTGGAACCTCGGCTGTGGTCGAGATCATCTCGGACACT
      K  F  T  K  E  L  F  V  G  D  Q  I  S  L  P  K  D  V  G  T  S  A  V  V  E  I  I  S  D  T

451  GAACTGATTGTCAAGAAAGAGTTCAAGGAGCTCAAGGCACTGGAGCTTTTAACCAGTGCTGAGGGATCCAAGTACAAGTGCATGCCTCAC
      E  L  I  V  K  K  E  F  K  E  L  K  A  L  E  L  L  T  S  A  E  G  S  K  Y  K  C  M  P  H

541  ATGGACCAGAGCAAGGTCTACAAGACTGTTTTTGAACGCTTAAATGCTGGCCATTGTGTTGGCATCTTTCCTGAAGGAGGTTCACACGAT
      M  D  Q  S  K  V  Y  K  T  V  F  E  R  L  N  A  G  H  C  V  G  I  F  P  E  G  G  S  H  D

631  CGTGCAGAGATGCTGCCCCTGAAAGCTGGTGTCACCATCATGGCGCTTGGCGCACTGGCCGCTAACCCTGACCTGGACCTTAAAATTGTG
      R  A  E  M  L  P  L  K  A  G  V  T  I  M  A  L  G  A  L  A  A  N  P  D  L  D  L  K  I  V

721  ACCTGCGGCCTGAACTATTTCCACCCCCATCGATTCCGTTCTCGCGCCGTTGTTGAGTTTGGTGAGCCTTTGACCGTGCCTCCAGAACTT
      T  C  G  L  N  Y  F  H  P  H  R  F  R  S  R  A  V  V  E  F  G  E  P  L  T  V  P  P  E  L

811  GTCGAGATGTACAAGAGGGGTGGAGCTGAGAAGCGCGAGGCCTGCGGAAAGCTCCTCGACACCATCTACGATGCACTCAAGAATGTCACA
      V  E  M  Y  K  R  G  G  A  E  K  R  E  A  C  G  K  L  L  D  T  I  Y  D  A  L  K  N  V  T

901  CTGAACGCCCCCGATTACGAAACACTCATGGTTATTCAAGCTGCCCGCCGTCTCTACAAGCCAACACATCGCAAGCTGCAGATCTCTCAA
      L  N  A  P  D  Y  E  T  L  M  V  I  Q  A  A  R  R  L  Y  K  P  T  H  R  K  L  Q  I  S  Q

991  GTTGTGGAGTTGAACCGTCGCTTCGTCGCTGGTTATCTGCACTTTCAGGACAACCCAAAGGTGATTGATACAAAGGACAAAGTTATGCAC
      V  V  E  L  N  R  R  F  V  A  G  Y  L  H  F  Q  D  N  P  K  V  I  D  T  K  D  K  V  M  H

1081  TACAACACTCAGCTACGCTATCATGGACTTCGCGACCACCAGGTCAACATCCGCACAACTCGGCGACATGCCATTGAACTATTGATTTGG
      Y  N  T  Q  L  R  Y  H  G  L  R  D  H  Q  V  N  I  R  T  T  R  R  H  A  I  E  L  L  I  W

1171  CGAGTTGTGCAGATGGTCTTTTTGAGTCTACTAGCGCTTCCAGGTACCATGATGAATCTTCCAGTTGCCATCGTTGCTCGCATCATCAGC
      R  V  V  Q  M  V  F  L  S  L  L  A  L  P  G  T  M  M  N  L  P  V  A  I  V  A  R  I  I  S

1261  AACAAGAAGGCCAAGGAGGCTTTGGCTGCATCGACCGTGAAAATTGCAGGAAGGGACGTTCTAGCCACATGGAAGTTGCTTGTGGCCCTG
      N  K  K  A  K  E  A  L  A  A  S  T  V  K  I  A  G  R  D  V  L  A  T  W  K  L  L  V  A  L

1351  GGATTGATGCCCGTCCTTTACTTTTCGTACTCGTTTGTTATCTTTTTGCTGTGTGGACGGTTCGACATTACGCTCAAGACCCGCCTCCTG
      G  L  M  P  V  L  Y  F  S  Y  S  F  V  I  F  L  L  C  G  R  F  D  I  T  L  K  T  R  L  L

1441  ATCGCTTGGGCGGCTTGGGCCTGCATTCCGTTTGTGACCTACGCCAGTATCCGTTTCGGTGAGGTGGGTATCGATATCTTCAAGTCGATC
      I  A  W  A  A  W  A  C  I  P  F  V  T  Y  A  S  I  R  F  G  E  V  G  I  D  I  F  K  S  I
```

```
1531  CGTCCTCTCTTCTTGTCAATCATTCCGGGCGAGGAAAACACGATCAATGAGCTCCGCAAGTCGGTGCAGAGCTTCAAAAGACCATCAAC
       R  P  L  F  L  S  I  I  P  G  E  E  N  T  I  N  E  L  R  K  S  R  A  E  L  Q  K  T  I  N

1621  GAGCTCATCAATGAGCTGGCCCCGGCCGGAAATATACCCGACTTTGATTCCAAACGAATCTTGGACCCCTTGCCAAACGATCGACCCAGCCGC
       E  L  I  N  E  L  A  P  E  I  Y  P  D  F  D  S  K  R  I  L  D  P  S  P  N  D  R  P  S  R

1711  GGGCGGTCGGCGGCTCCGGCCTCGGGGACCTTGCGCAGACCATTTTCAACACCATGAACACGGCCACACAGCCGCTAAACCAATGGCTC
       G  A  S  R  S  A  S  G  T  N  L  A  Q  T  I  F  N  T  M  N  T  A  T  Q  P  L  N  Q  W  L

1801  GGTATGGATGGGCGCTTCGAGTGGGAGCGTGTGGACGACTCGGATGCGGACGACGTGTTCTTTTTCCTCAACCCTGCAGGAGCCATCCAA
       G  M  D  G  R  F  E  W  E  R  V  D  D  S  D  A  D  D  V  F  F  F  L  N  P  A  G  A  I  Q

1891  GGGCGATCGAGGACGTCTCTTGGGGTGCTCAGGGCAGATTCAGCTGGGCGAAGGGTTCAAGCTGGAAGCTGGAGGCATTGACAGAGCTGCCAAAGGAGTGGCAGT
       G  R  S  R  T  S  S  W  G  A  G  A  W  T  P  S  S  A  G  D  G  S  R  S  R  S  R  S  R  S

1981  CGGACCGAGCTCGTTGCGTCAGGGCAGATTCAGCTCAGGTTCAAGCTGGAGGCATTGACAGAGCTGCCAAAGGATAAGCCTTTT
       R  T  S  S  F  A  S  G  Q  I  Q  L  G  E  G  F  K  L  E  A  L  T  E  L  P  K  D  K  P  F

2071  GGGCGAGGTGACACCGACGACTCAGTGGCAAGACAGAAGCATGGTGGGCGACATGACCAAGGATCCCGAGGAGATTGAGAAG
       G  E  V  T  R  R  L  S  L  S  R  K  Q  K  H  G  L  V  G  D  M  T  K  D  P  E  E  I  E  K

2161  CAGGGGCGGATTTATGCATGAGGGACACTTTGTCAGCACAACCCCGCCCATCACGGTTCAGAACATGGATGATCCTATGGATGCAGTCAAGTCT
       Q  G  G  F  M  H  E  G  H  F  V  S  T  P  P  I  T  V  Q  N  M  D  D  P  M  D  A  V  K  S

2251  AAGGAGGCATAA
       K  E  A
```

```
                1                                                                                                   100
MaGPAT3         ------------------------------------MGLQIYDFVSFFFTLLLDIFFREIRPRGAHKIPRQG-PVIFVAAPHANQEVDPLV
MaGPAT1         ------------------------------------MALQIYDFVSFFFTILLDIFFREIRPPGAHKIPQKG-PVIFVAAPHANQEVDPLV
ScSCT1          MPAPKLTEKFASSKSTQKTTNYSSIEAKSVKTSADQAYIYQEPSATKKILSIATWLLYNIFHCFFREIRGRSSFKVPQDG-PVIFVAAPHANQEVDRVI
ScGPT2          ---------------MSAPAADHNAAKPIPHVPQASRRYKNSYNGFVYNIHTWLYDVSVFLFNILFTIFFREIKVRGAYNVPEVGVPTLVCAPHANQEIDDAL
                                                                                * *

101                                                                                                 200
MaGPAT3         LMRECG-----------RVSFLAAKKSMDRRWLGAMARSMNAIPVERPQDLAKAGSGTIKLVDR--------YGDPLRITGLGTKFTKELFVGDQIS
MaGPAT1         LMRECG-----------RVSFLAAKKSMDRRWLGAMARSMNAIPVERPQDLAKAGSGVIKLLDR--------YGDPLRVTGVGTKFTKELLVGDQIS
ScSCT1          LMGEVKKSVN-------RRVSFLIAESQLKQPPIGFLASFFMAIGVVRPDDNLKPAEGTIRVDP--------TDYKRVIGHDTHFLTDCMPKGLIG
ScGPT2          VMSQTRLLKTSAGKSRSRMPCFVTAESSFKKRFLSFFGHAMGGIPVFRIDDNLKPVDENLEIYAPDLKNHPEIIKGRSKNPQTTPVNETKRFSAKSLLG
                                                                                                                  +

201                                                                                                 300
MaGPAT3         PKDVGTSAVVEIISQTELIVKKEEKELKALELLTSAEGSKYKCMPHMDQSKVYKTVFERLNAGHCVGIFPEGGSHDRAEMLPLKAGVTIMALGALAANPD
MaGPAT1         PKDVGSSAVVEIISQTELIVKKEEKELKALELLTSPDGTKYKCLPHMDQTNVYKTVFERLNAGHCVGIFPEGGSHDRAEMLPLKAGVTIMALGALAANPS
ScSCT1          PKSMGFGEIQSIESQTSLTLRKEEKMAKPEIKTALLTGTTYKYAAKVDQSCVYHRVFEHLAHNNCIGIFPEGGSHDRTNLLPLKAGVAIMALGCMDKHPD
ScGPT2          PDYLSNAQIKELPDQETIILSSPERTSKSKVVELLTNGTNFKYAEKIDNTETFQSVFDHLHTKGCVGIFPEGGSHDRPSLLPIKAGVAIMALGAVAADPT
                                                                                    * +

301                                                                                                 400
MaGPAT3         LDLKIVTCGLNYFHPHRFRSRAVVEFGEPLTVPPELVEMYKRGGAEKREACGKLEDTIYDALKNVTLNAPDYETLMVIGAARRLYKPTHR-KEQISQVVE
MaGPAT1         LDLKINTCGLNYFHPHRFRSRAVVEFGEPLTVPPELVEMYKRGGAEKREACGKLEDTIYEALRGVTLNAPDYETLMVIGAARRLYKPTHR-KEQISQVVE
ScSCT1          VNVKIVPCGMNYFHPHKFRSRAVVEFGDPIEIPKELVAKYHN-PETNRDAVKELEDTISKGLQSVTVTCSDYETLMVVITIPRLYMTQFSTKLPLPLIVE
ScGPT2          MKVAVVPCGLHYFHRNKFRSRAVLEYGEPIVVDGKYGEMYKD---SPRETVSKLLKKITNSLFSVZENAPYDTLMVIGAARRLYQPVKV-RLPLPAIVE
                  *

401                                                                                                 500
MaGPAT3         LNRRFVAGYLHFQDNPKVIDTKDKVMHYNTQLRYHGLRDHQVN-IRTTRRHAIE----LLIWRVQMVFLSLLCALPGTMMNLPVAIVARIISNKKAKEALA
MaGPAT1         LNRRFVAGYMHFKDNPKVIEAKDKVMHYNTQLRYHGLRDHQVN-IRTTRKHAIG----MLISRLIQMIFLSCLALPGTLMNLPVAIVARVISNKKAKEALA
ScSCT1          MNVRPMVKGYEFYRNDPKIADLTKDIMAYNAALRHYNLPDHLVEEAKVNFAKNLG---LVFFRSIGLCILFSLAMPGIIMFSPVFILAKRISQEKARTALS
ScGPT2          INRRLLFGISKFKDDPRIIHLKKLVYDYNRKLDSVGLKDHQWMQLKTTKLEALRCFVTLIVRLIKFSVFAILSLPGSILFTPIFIICRVYSEKKAKEGLK 501                                                                                                 600
MaGPAT3         ASTVKIAGRDVLATWKLLVALGLMPVLYFSYSFVIFLLCGR------FDITLKTRLLIAWAAWACIPFVTYASIRFGEVGIDIFKSIRPLFLSIIPGEENT
MaGPAT1         ASTVKIAGRDVLATWKLLVALGLMPVLYFTYSVMVFIYCGR------FDISFKSRLLIAWAAWALIPFVTYASIRFGEVGIDIFKSIRPLFLSIIPGEEST
ScSCT1          KSTVKIKANDVIATWKILIGMGFAPLYIFWSVLITYYLR--------HKPWN-KIYVFSGSYICVIVTYSALIVGDIGMDGFKSLRPLVLSLTSPKG---
ScGPT2          KSLVKIKGTTDLLATWALIVALILAPILYVTYSILLIIFARLARKQHYCRIWVPSNNAFIQFVYFYALLVFTIYSSLKTGEIGVQLFKSLRPLFVSIVYPGKK- 601                                                                                                 700
MaGPAT3         INELRKSRAELQKTINELINELAPEIYPDFSKRILDPSPNDRPSRGASRSASGTNLAQTIFNTMNTATQPLNQWLGMDGRFEWERVDDSDADDVFFFLN
MaGPAT1         INDLRKAEAELQKTITNLINELAPQIYPDFSKRILDPSPADRPSR----SASGTNLAQTIFN----TAAQPLNQWLGKDGRFEWERTEDSDADDVFFFLD
ScSCT1          LQKLQKDERNLAERIIEVVNNFGSELFPDFSAALREEFQVIDEEE-------EDR--KTSELN----RRKMLRKQKIKRQEKDSSSPIISQRDNHDAYEH
ScGPT2          IEEIQTTRKNLSLELTAVCNDLGPLVFDYDKLATEIFSKRDGYDVS----S---------------DAESSISRMSVQSRSRSSS-----------IHSI 701                                                                                                 800
MaGPAT3         PAGAIQGRSRTSSWGAGAWTPSSAGDGSR-SRSRSRSRTSSFASGQIQLGEGFKLEALTELPKDKPFGEVTRRLSLSRKQHGLVGDMTKDPEEIEKQGG
MaGPAT1         PARGILGRSRASSWGGGAFTEAADGS-------RSRNRSRTSSFTSGQIQLGEGFKLEALTELPRDKPFAEVTRRLSVSRMQRYGLEGMTRSDTDENE--G-
ScSCT1          HNQDSDGVSLVNSDNSLSNIPLFSSTFHRKSESSLASTSVAPSSSSEFEVNEILEEKNGLASKIAQAVLNKRIGENTAREEEEEEEEEEEEEEEEEEG-
ScGPT2          GSLASNALSRVNSRGSLTDIPIFSDAK-----QGQWKSEGETSEDEDEFDEKNPAIVQTARSSDLNKENSRNTNISSKIASLVRQKREHEKKE- 801           830
MaGPAT3         FMHEGHFVSTPPITVQNMDDPMDAVKSKEA
MaGPAT1         -------------------------STAKSKDI
ScSCT1          -------------------------KEGDA
ScGPT2          ---------------------------------
```

GLYCEROL-3-PHOSPHATE ACYL TRANSFERASE

SEQUENCE LISTING

The instant application contains a Sequence Listing which has been submitted in ASCII format via EFS-Web and is hereby incorporated by reference in its entirety. Said ASCII copy, created on May 15, 2013, is named P41462_SL.txt and is 57,257 bytes in size.

TECHNICAL FIELD

The present invention relates to a polynucleotide encoding a novel glycerol-3-phosphate acyltransferase and use thereof.

BACKGROUND ART

Fatty acids are important components of lipids such as phospholipids, triacylglycerols, etc. Fatty acids containing two or more unsaturated bonds are collectively referred to as polyunsaturated fatty acids (PUFA) are known to specifically include arachidonic acid, dihomo-γ-linolenic acid, eicosapentaenoic acid, docosahexaenoic acid, etc. Some of these polyunsaturated fatty acids cannot be synthesized in the animal body. Thus, it is necessary to take such polyunsaturated fatty acids as essential amino acids through food.

In the animal body, polyunsaturated fatty acids are distributed in a wide variety of organs and tissues. For example, arachidonic acid has been separated from lipids extracted from the animal adrenal gland or liver. However, polyunsaturated fatty acids are contained in small quantities in the animal organs, and the extraction and separation of polyunsaturated fatty acids from the animal organs are not sufficient to supply a large quantity of polyunsaturated fatty acids. For this reason, methods of acquiring polyunsaturated fatty acids by culturing various microorganisms have been developed. Among those microorganisms, a Mortierella microorganism is known as a microorganism capable of producing lipids containing polyunsaturated fatty acids such as arachidonic acid, etc. Furthermore, an attempt to produce polyunsaturated fatty acids in plants has also been made. Polyunsaturated fatty acids constitute storage lipids such as triacylglycerols, etc. and are known to be accumulated within the cells of microorganisms or in the seeds of plants.

Triacylglycerols, which are storage lipids, are produced in vivo as follows. Acyl transfer occurs on glycerol-3-phosphate by glycerol-3-phosphate acyltransferase to form lysophosphatidic acid. Next, acyl transfer further occurs by lysophosphatidic acid acyltransferase to form phosphatidic acid. This phosphatidic acid is, in turn, dephosphorylated by phosphatidic acid phosphatase to form diacylglycerol. Finally, acyl transfer occurs by diacylglycerol acyltransferase to form triacylglycerol.

In the triacylglycerol biosynthesis pathway or the phospholipid biosynthesis pathway described above, it is known that the acylation reaction of glycerol-3-phosphate to form lysophosphatidic acid is mediated by glycerol-3-phosphate acyltransferase (hereinafter sometimes referred to as "GPAT"; EC 2.3.1.15).

The presence of GPAT genes has been reported so far in several organisms. As mammalian GPAT genes, two types of microsome (membrane-bound) and mitochondria (membrane-bound) have been cloned (Non-Patent Literature 2). Likewise, three types of microsome (membrane-bound), mitochondria (membrane-bound) and chloroplast (free) have also been cloned as plant GPAT genes (Non-Patent Literature 3).

As the GPAT genes derived from the fungus *Saccharomyces cerevisiae*, two types of microsomal (membrane-bound) GPT2/GAT1 (YKR067w) and SCT1/GAT2 (YBL011w) have been cloned; it is known that simultaneous deletion of both genes results in lethality (Non-Patent Literature 4). In these fungal genes, it is shown that GPT2 has the activity to use a wide range of fatty acids from palmitic acid (16:0) to oleic acid (18:1) as substrate, whereas SCT1 has a strong selectivity in using 16 carbon fatty acids such as palmitic acid (16:0) and palmitoleic acid (16:1)) as substrate (Non-Patent Literature 4).

Furthermore, the GPAT genes have also been cloned from many other organism species. Above all, the GPAT derived from the microorganisms of the genus Mortierella capable of producing lipids is reported as follows.

In the GPAT derived from *Mortierella ramanniana*, microsomal GPAT has been isolated and shown to be used as an acyl donor with a 5.4-fold higher selectivity of oleic acid (18:1) than palmitic acid (16:0) (Non-Patent Literature 5). It is reported that the GPAT derived from *Mortierella alpina* (hereinafter sometimes referred to as "*M. alpina*" has a glycerol-3-phosphate acyltransferase activity in its microsomal fraction (Non-Patent Literature 6).

It is shown that when the GPAT present in the microsome of *M. alpina* (in a membrane-bound state) is reacted in vitro with various acyl CoAs, the GPAT uses as substrate a broad range of polyunsaturated fatty acids including oleic acid (18:1), linoleic acid (18:2), dihomo-γ-linolenic acid (DGLA) (20:3) and arachidonic acid (20:4) (Patent Literature 1).

It is shown that when the GPAT cloned from *M. alpina* (ATCC #16266) (hereinafter referred to as MaGPAT1 (ATCC#16266)) was expressed in transformant *Yarrowia lipolytica* designed to enable biosynthesis to give eicosapentaenoic acid (EPA), in total fatty acids, the composition of dihomo-γ-linolenic acid (DGLA) (20:3) increased and the composition of oleic acid (18:1) decreased. The results indicate that polyunsaturated fatty acid with a longer chain length and high degree of unsaturation is selectively incorporated (Patent Literature 2).

In recent years, it is reported that GPAT homologue or MaGPAT2 was isolated from *M. alpina* (1S-4) and showed the substrate specificity different from MaGPAT1 (Patent Literature 3). That is, it is suggested that MaGPAT1 would show high specificity to palmitic acid and MaGPAT2 would show high specificity to oleic acid.

RELATED ART

Patent Literatures

[Patent Literature 1] Pamphlet of WO 2004/087902
[Patent Literature 2] US 2006/0094091
[Patent Literature 3] Pamphlet of WO 2008/156026

Non-Patent Literatures

[Non-Patent Literature 1] Lipids, 39, 1147 (2004)
[Non-Patent Literature 2] Biochimica et Biophysica Acta, 1348, 17-26, 1997
[Non-Patent Literature 3] Biochimica et Biophysica Acta, 1348, 10-16, 1997
[Non-Patent Literature 4] The Journal of Biological Chemistry, 276 (45), 41710-41716, 2001

[Non-Patent Literature 5] The Biochemical Journal, 355, 315-322, 2001

[Non-Patent Literature 6] Biochemical Society Transactions, 28, 707-709, 2000

DISCLOSURE OF THE INVENTION

Under the foregoing circumstances, it has been desired to develop a novel GPAT homologue contributing to further activation of and efficient fatty acid synthesis pathway by efficiently producing lysophosphatidic acid and triacylglycerols formed based thereon.

As a result of extensive investigations, the present inventors have succeeded in cloning a gene encoding the third GPAT homologue (MaGPAT3) of lipid-producing fungus *M. alpina* and accomplished the present invention. That is, the present invention provides the following polynucleotides, proteins, expression vectors, transformants, method for producing food, etc. using the transformants, foods, etc. produced by the method, and so on.

That is, the present invention provides the following features.

[1] A polynucleotide of any one selected from the group consisting of (a) to (e) below:

(a) a polynucleotide comprising the nucleotide sequence of SEQ ID NO: 1 or 4;

(b) a polynucleotide encoding a protein consisting of the amino acid sequence of SEQ ID NO: 2;

(c) a polynucleotide encoding a protein consisting of an amino acid sequence wherein 1 to 100 amino acids are deleted, substituted, inserted and/or added in the amino acid sequence of SEQ ID NO: 2, and having a glycerol-3-phosphate acyltransferase activity;

(d) a polynucleotide encoding a protein having an amino acid sequence having at least 85% homology to the amino acid sequence of SEQ ID NO: 2, and having a glycerol-3-phosphate acyltransferase activity; and, (e) a polynucleotide which hybridizes to a polynucleotide consisting of a nucleotide sequence complementary to the nucleotide sequence of SEQ ID NO: 1 or 4 under stringent conditions, and which encodes a protein having a glycerol-3-phosphate acyltransferase activity.

[2] The polynucleotide according to [1] above of any one as defined in (f) or (g) below:

(f) a polynucleotide encoding a protein consisting of an amino acid sequence wherein 1 to 10 amino acids are deleted, substituted, inserted and/or added in the amino acid sequence of SEQ ID NO: 2, and having a glycerol-3-phosphate acyltransferase activity; and, (g) a polynucleotide encoding a protein having an amino acid sequence having at least 90% homology to the amino acid sequence of SEQ ID NO: 2, and having a glycerol-3-phosphate acyltransferase activity.

[3] The polynucleotide according to [1] above, comprising the nucleotide sequence of SEQ ID NO: 1 or 4.

[4] The polynucleotide according to [1] above, encoding a protein consisting of the amino acid sequence of SEQ ID NO: 2.

[5] The polynucleotide according to any one of [1] to [4] above, which is a DNA.

[6] A protein encoded by the polynucleotide according to any one of [1] to [5] above.

[7] A vector comprising the polynucleotide according to any one of [1] to [5] above.

[8] A non-human transformant introduced with the polynucleotide according to any one of [1] to [5] above.

[9] A non-human transformant introduced with the vector according to [7] above.

[10] The transformant according to [8] or [9] above, wherein the transformant is a lipid-producing fungus.

[11] The transformant according to [10] above, wherein the lipid-producing fungus is *Mortierella alpina*.

[12] A method for producing a lipid or fatty acid composition, which comprises collecting the lipid or fatty acid composition from the culture of the transformant according to any one of [8] to [11] above.

[13] A food, pharmaceutical, cosmetic or soap comprising the lipid or fatty acid composition collected by the production method according to [12] above.

The polynucleotide of the present invention can be used for transformation of a lipid-producing fungus (e.g., *M. alpina*), yeast, plant, etc., and the lipid-producing fungus transformants, yeast transformants, plant transformants, etc., thus produced can be used to produce fatty acid compositions, foods, cosmetics, pharmaceuticals, soaps, etc.

More specifically, the transformants of the present invention provide an extremely high production efficiency of triglycerides, and a large part of fatty acids increased in the transformants are due to an increase of fatty acids in the triglycerides. Accordingly, these transformants can be effectively used to manufacture medicaments or health foods.

BRIEF DESCRIPTION OF THE DRAWINGS

FIG. 1-1 shows the alignment between the genome sequence and CDS sequence of MaGPAT3e.

FIG. 1-2 is continued from FIG. 1-1.

Figure 3:
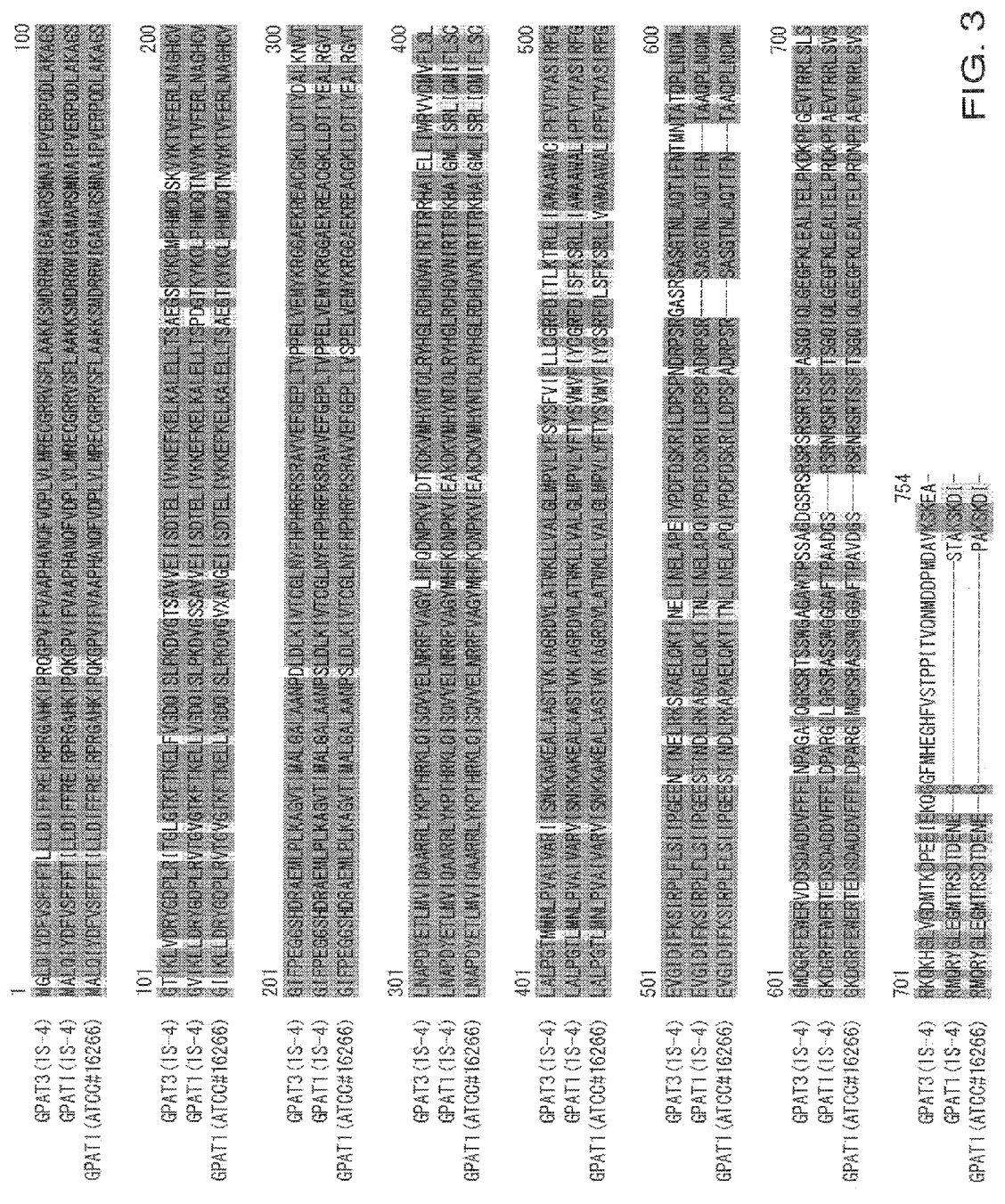

FIG. 1-3 is continued from FIG. 1-2. FIGS. 1-1 to 1-3 disclose the genome sequence as SEQ ID NO: 4 and the CDS sequence as SEQ ID NO: 3.

FIG. 2-1 shows the CDS sequence and putative amino acid sequence of MaGPAT3 (1S-4).

FIG. 2-2 is continued from FIG. 2-1. FIGS. 2-1 to 2-2 disclose the CDS sequence as SEQ ID NO: 3 and the putative amino acid sequence as SEQ ID NO: 2.

FIG. 3 shows the alignment of amino acid sequences between MaGPAT1 ((1S-4) and (ACTT#16266)) and MaGPAT3 (1S-4) (SEQ ID NOS 17, 18, and 2, respectively).

FIG. 4 shows the alignment of amino acid sequences among various GPAT homolog proteins (MaGPAT1, MaGPAT3, ScSCT1 and ScGPT2) (SEQ ID NOS 17, 2, 19, and 20, respectively). The four domains conserved in the GPAT homologs and the amino acid residues (asterisks) considered to be important for the GPAT activity and the amino acid residues (crosses) considered to be important for binding to glycerol-3-phosphate, in these domains were conserved also in GPAT3.

BEST MODE FOR CARRYING OUT THE INVENTION

Hereinafter the present invention is described in detail. The embodiments below are intended to be merely by way of example only to describe the invention but not limited only to these embodiments. The present invention may be implemented in various ways without departing from the gist of the invention.

All of the publications, published patent applications, patents and other patent literatures cited in this application are herein incorporated by reference in their entirety. This application hereby incorporates by reference the contents of the specification and drawings in Japanese Patent Application No. 2009-217646 filed Sep. 18, 2009, from which the priority was claimed.

The present inventors have succeeded for the first time in cloning the gene of the full-length cDNA of gene (MaGPAT3) encoding the third glycerol-3-phosphate acyltransferase homolog of lipid-producing fungus *M. alpina*, as will be later described in detail in EXAMPLES. The present inventors have also identified the nucleotide sequence of genomic DNA of MaGPAT3 from *M. alpina* and its putative amino acid sequence. The ORF sequence of MaGPAT3, the putative amino acid sequence of MaGPAT3, the CDS sequence of MaGPAT3 and the genome sequence of MaGPAT3 are SEQ ID NO: 1, SEQ ID NO: 2, SEQ ID NO: 3 and SEQ ID NO: 4, respectively. The genome sequence of MaGPAT1 from *M. alpina* is also shown in SEQ ID NO: 5. These polynucleotides and enzymes may be obtained by the methods described in EXAMPLES below, known genetic engineering techniques, known methods for synthesis, and so on.

1. Polynucleotide of the Invention

First, the present invention provides the polynucleotide described in any one selected from the group consisting of (a) to (e) below:

(a) a polynucleotide comprising the nucleotide sequence of SEQ ID NO: 1 or 4;

(b) a polynucleotide encoding a protein consisting of the amino acid sequence of SEQ ID NO: 2;

(c) a polynucleotide encoding a protein consisting of an amino acid sequence wherein 1 to 100 amino acids are deleted, substituted, inserted and/or added in the amino acid sequence of SEQ ID NO: 2, and having a glycerol-3-phosphate acyltransferase activity;

(d) a polynucleotide encoding a protein having an amino acid sequence having at least 85% homology to the amino acid sequence of SEQ ID NO: 2, and having a glycerol-3-phosphate acyltransferase activity; and, (e) a polynucleotide which hybridizes to a polynucleotide consisting of a nucleotide sequence complementary to the nucleotide sequence of SEQ ID NO: 1 or 4 under stringent conditions, and which encodes a protein having aglycerol-3-phosphate acyltransferase activity.

As used herein, the term "polynucleotide" means a DNA or RNA.

As used herein, the term "polynucleotide which hybridizes under stringent conditions" refers to a polynucleotide obtained by a colony hybridization method, a plaque hybridization method, a Southern hybridization method or the like, using as a probe, for example, a polynucleotide consisting of a nucleotide sequence complementary to the nucleotide sequence of SEQ ID NO: 1 or 4, or the whole or part of a polynucleotide consisting of the nucleotide sequence encoding the amino acid sequence of SEQ ID NO: 2. For the methods of hybridization, there are used the methods described in, e.g., "Sambrook & Russell, Molecular Cloning; A Laboratory Manual Vol. 3, Cold Spring Harbor, Laboratory Press 2001" and "Ausubel, Current Protocols in Molecular Biology, John Wiley & Sons 1987-1997", etc.

As used herein, the term "stringent conditions" may be any of low stringent conditions, moderate stringent conditions or high stringent conditions. The term "low stringent conditions" are, for example, 5×SSC, 5×Denhardt's solution, 0.5% SDS, 50% formamide at 32° C. The term "moderate stringent conditions" are, for example, 5×SSC, 5×Denhardt's solution, 0.5% SDS, 50% formamide at 42° C. The term "high stringent conditions" are, for example, 5×SSC, 5×Denhardt's solution, 0.5% SDS, 50% formamide at 50° C. Under these conditions, a DNA with higher homology is expected to be obtained efficiently at higher temperatures, although multiple factors are involved in hybridization stringency including temperature, probe concentration, probe length, ionic strength, time, salt concentration and others, and one skilled in the art may appropriately select these factors to achieve similar stringency.

When commercially available kits are used for hybridization, for example, Alkphos Direct Labeling and Detection System (GE Healthcare) may be used. In this case, according to the attached protocol, after incubation with a labeled probe overnight, the membrane is washed with a primary wash buffer containing 0.1% (w/v) SDS at 55° C., thereby detecting hybridized DNA.

In addition to those described above, other polynucleotides that can be hybridized include DNAs having 74% or higher, 75% or higher, 76% or higher, 77% or higher, 78% or higher, 79% or higher, 80% or higher, 81% or higher, 82% or higher, 83% or higher, 84% or higher, 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher or 99.9% or higher homology to the DNA of SEQ ID NO: 1 or 4, or the DNA encoding the amino acid sequence of SEQ ID NO: 2, as calculated by homology search software, such as FASTA and BLAST using default parameters.

Homology between amino acid sequences or nucleotide sequences may be determined using algorithm BLAST by Karlin and Altschul (Proc. Natl. Acad. Sci. USA, 87: 2264-2268, 1990; Proc. Nail Acad. Sci. USA, 90: 5873, 1993). Programs called BLASTN and BLASTX based on the BLAST algorithm have been developed (Altschul S. F. et al., J. Mol. Biol. 215: 403, 1990). When a nucleotide sequence is sequenced using BLASTN, the parameters are, for example, score=100 and wordlength=12. When an amino acid sequence is sequenced using BLASTX, the parameters are, for example, score=50 and wordlength=3. When BLAST and Gapped BLAST programs are used, default parameters for each of the programs are employed.

The polynucleotides of the present invention described above can be acquired by known genetic engineering techniques, known methods for synthesis, and so on.

2. Protein of the Invention

The present invention provides the proteins shown below.

(i) A protein encoded by the polynucleotide of any one of (a) to (e) above.

(ii) A protein comprising the amino acid sequence of SEQ ID NO: 2.

(iii) A protein containing an amino acid sequence wherein one or more amino acids are deleted, substituted, inserted and/or added in the amino acid sequence of SEQ ID NO: 2, and having a glycerol-3-phosphate acyltransferase activity.

(iv) A protein having an amino acid sequence having at least 85% homology to the amino acid sequence of SEQ ID NO: 2, and having a glycerol-3-phosphate acyltransferase activity.

The proteins described in (iii) or (iv) above are typically mutants of the naturally occurring protein of SEQ ID NO: 2 and include those proteins which may be artificially obtained using site-directed mutagenesis described in, e.g., "Sambrook & Russell, Molecular Cloning: A Laboratory Manual, Vol. 3, Cold Spring Harbor Laboratory Press 2001," "Ausubel, Current Protocols in Molecular Biology, John Wiley & Sons 1987-1997," "Nuc. Acids. Res., 10, 6487 (1982)," "Proc. Natl. Acad. Sci. USA, 79, 6409 (1982),"

"Gene, 34, 315 (1985)," "Nuc. Acids. Res., 13, 4431 (1985)," "Proc. Natl. Acad. Sci. USA, 82, 488 (1985)," etc.

As used herein, "the protein containing an amino acid sequence wherein one or more amino acids are deleted, substituted, inserted and/or added in the amino acid sequence of SEQ ID NO: 2, and having a glycerol-3-phosphate acyltransferase activity" includes proteins containing an amino acid sequence wherein, e.g., 1 to 100, 1 to 90, 1 to 80, 1 to 70, 1 to 60, 1 to 50, 1 to 40, 1 to 39, 1 to 38, 1 to 37, 1 to 36, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9 (1 to several), 1 to 8, 1 to 7, 1 to 6, 1 to 5, 1 to 4, 1 to 3, 1 to 2, or one amino acid is/are deleted, substituted, inserted and/or added in the amino acid sequence of SEQ ID NO: 2, and having the glycerol-3-phosphate acyltransferase activity. In general, the number of deletions, substitutions, insertions, and/or additions is preferably smaller.

Such proteins include a protein having an amino acid sequence having a homology of approximately 85% or higher, 86% or higher, 87% or higher, 88% or higher, 89% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher, to the amino acid sequence of SEQ ID NO: 2, and having the glycerol-3-phosphate acyltransferase activity. As the homology percentage described above is higher, the protein is more preferable in general.

The glycerol-3-phosphate acyltransferase activity can be assayed, e.g., by the method described in J. B. C. 276 (45), 41710-41716 (2001). To verify the GPAT activity, there is a complementation experiment using the Δgpt2 and Δsct 1 strains of yeast. When a polynucleotide encoding the enzyme is expressed in the Δgpt2 and Δsct1 strains (simultaneous deletion of GPT2 and SCT1 results in lethality) and the Δgpt2 and Δsct1 strains are capable of growing, the protein or peptide encoded by the polynucleotide is found to have the GPAT activity.

The deletion, substitution, insertion and/or addition of one or more amino acid residues in an amino acid sequence of the protein of the invention means that one or a plurality of amino acid residues are deleted, substituted, inserted and/or added at one or a plurality of positions in the same amino acid sequence. Two or more types of deletions, substitutions, insertions and additions may occur concurrently.

Examples of the amino acid residues which are mutually substitutable are given below. Amino acid residues in the same group are mutually substitutable. Group A: leucine, isoleucine, norleucine, valine, norvaline, alanine, 2-aminobutanoic acid, methionine, o-methylserine, t-butylglycine, t-butylalanine and cyclohexylalanine; Group B: aspartic acid, glutamic acid, isoaspartic acid, isoglutamic acid, 2-aminoadipic acid and 2-aminosuberic acid; Group C: asparagine and glutamine; Group D: lysine, arginine, ornithine, 2,4-diaminobutanoic acid and 2,3-diaminopropionic acid; Group E: proline, 3-hydroxyproline and 4-hydroxyproline; Group F: serine, threonine and homoserine; and Group G: phenylalanine and tyrosine.

The protein of the present invention may also be produced by chemical synthesis methods such as the Fmoc method (fluorenylmethyloxycarbonyl method), the tBoc method (t-butyloxycarbonyl method), etc. In addition, peptide synthesizers available from Advanced Automation Peptide Protein Technologies, Perkin Elmer, Protein Technology Instrument, PerSeptive, Applied Biosystems, SHIMADZU Corp., etc. may also be used for the chemical synthesis.

3. Vector of the Invention and Transformant Introduced With the Vector

In another embodiment, the present invention also provides the expression vector comprising the polynucleotide of the invention.

The vector of the invention is generally constructed to contain an expression cassette comprising:

(i) a promoter that can be transcribed in a host cell;

(ii) any of the polynucleotides described in (a) to (g) above that is linked to the promoter; and, (iii) a signal that functions in the host cell with respect to the transcription termination and polyadenylation of RNA molecule. The vector thus constructed is introduced into a host cell. Examples of host cells which may be appropriately used in the present invention include lipid-producing fungi, yeast, and the like.

The lipid-producing fungi which can be used are the strains described in, e.g., MYCOTAXON, Vol. XLIV, No. 2, pp. 257-265 (1992). Specific examples include microorganisms belonging to the genus *Mortierella* including microorganisms belonging to the subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70 and CBS754.68, etc., or microorganisms belonging to the subgenus *Micromucor*, e.g., *Mortierella isabellina* CBS194.28, IFO6336, IFO7824, IFO7873, IFO7874, IFO8286, IFO8308 and IFO7884, *Mortierella nana* IFO8190, *Mortierella ramanniana* IFO5426, IFO8186, CBS112.08, CBS212.72, IFO7825, IFO8184, IFO8185 and IFO8287, *Mortierella vinacea* CBS236.82, etc. Among others, *Mortierella alpina* is preferable.

Examples of the yeast are *Saccharomyces cerevisiae* NBRC1951, NBRC1952, NBRC1953, NBRC1954, etc.

In introducing the vector of the invention into the yeast and assaying the glycerol-3-phosphate acyltransferase activity of GPAT3 protein encoded by the vector, deficiency of the GPAT genes (Gpt2p and Sct1p) of yeast used as a host cell enables to assess the enzyme activity only of the GPAT3 protein. Accordingly, in an embodiment of the invention, the yeast as a host cell is preferably deficient of the Gpt2p gene and the Sct1p gene.

These host cells transformed by the vector of the invention produce larger amounts of triglycerides than host cells which are not transformed by the vector of the invention. A large part of the fatty acids are fatty acids that constitute triglycerides increased by introducing the vector of the invention.

Vectors used to introduce into the lipid-producing fungi include but not limited to, for example, pDura5 (Appl. Microbiol. Biotechnol., 65, 419-425, (2004)).

As vectors which may be used for introduction into the yeast, any vector is usable and not particularly limited as far as it is a vector having the activity of expressing the insert in the yeast cells, and includes, e.g., pYE22m (Biosci. Biotech. Biochem., 59, 1221-1228, 1995).

Promoters/terminators for regulating gene expression in host cells may be in any combination as far as they function in the host cells. For example, a promoter of the histone H4.1 gene, a promoter of the glyceraldehyde-3-phosphate dehydrogenase, etc. can be used.

As a selection marker used for the transformation, there may be used auxotrophic markers (ura5, niaD), chemical-resistant markers (hygromycin, zeocin), geneticin-resistant gene (G418r), copper-resistant gene (CUP1) (Marin et al., Proc. Natl. Acad. Sci. USA, 81, 337 1984), cerulenin-resistant gene (fas2m, PDR4) (Junji Inokoshi, et al., Biochemistry, 64, 660, 1992; and Hussain et al., Gene, 101: 149, 1991, respectively).

For transformation of host cells, there may be used generally known methods. For example, methods which may be used include but not limited to the electroporation method (Mackenxie D. A. et al., Appl. Environ. Microbiol., 66, 4655-4661, 2000), the particle delivery method (method described in JPA 2005-287403 "Method of Breeding Lipid-Producing Fungus"), the spheroplast method (Proc. Natl. Acad. Sci. USA, 75 p 1929 (1978)), the lithium acetate method (J. Bacteriology, 153 p 163 (1983)), and methods described in Proc. Natl. Acad. Sci. USA, 75 p 1929 (1978), Methods in yeast genetics, 2000 Edition: A Cold Spring Harbor Laboratory Course Manual, etc.

In addition, reference may be made to "Sambrook & Russell, Molecular Cloning: A Laboratory Manual Vol. 3, Cold Spring Harbor Laboratory Press 2001," "Methods in Yeast Genitics, A laboratory manual (Cold Spring Harbor Laboratory Press, Cold Spring Harbor, N.Y.)," etc. for general cloning techniques.

4. Method for Producing Lipid or Fatty Acid Composition of the Invention

In another embodiment, the present invention further provides a method for preparing a lipid or fatty acid composition which comprises using the lipid-producing fungus or yeast transformant described above.

As used herein, the term "lipid" is intended to mean a simple lipid including a compound (e.g., a glyceride) which is composed of a fatty acid and an alcohol attached via an ester linkage, or its analog (e.g., a cholesterol ester), etc.; a complex lipid in which phosphoric acid, amino acid(s), saccharide(s) or the like are bound to a part of the simple lipid; or a derived lipid which is a hydrolysate of the above lipid and is insoluble in water.

As used herein, the term "oil and fat" is intended to mean an ester of glycerol and a fatty acid (glyceride).

As used herein, the term "fatty acid" is intended to mean an aliphatic monocarboxylic acid (a carboxylic acid having one carboxylic group and carbon atoms connected to each other in a chain) represented by general formula RCOOH (wherein R is alkyl). The fatty acid includes a saturated fatty acid having no double bond and an unsaturated fatty acid containing double bonds in the hydrocarbon chain.

The lipid or fatty acid composition of the present invention can be extracted as follows, from the cells transformed according to the present invention. After completion of the incubation, the transformants of an organism (e.g., lipid-producing fungus or yeast) are treated in a conventional manner including centrifugation, filtration, etc. to yield culture cells. The cells are thoroughly washed with water and preferably dried. Drying may be performed by lyophilization, air drying, etc. The dried cells are disrupted in a Dyno mill or by ultrasonication, etc., if necessary, and then extracted with an organic solvent preferably in a nitrogen flow. The organic solvent which can be used includes ether, hexane, methanol, ethanol, chloroform, dichloromethane, petroleum ether, etc. Alternatively, good results can be obtained also by alternating extraction of methanol and petroleum ether, single phase extraction of chloroform-methanol-water. By removing the organic solvent by distillation under reduced pressure, the lipid containing fatty acids can be yielded. The fatty acids extracted may also be esterified by the hydrochloric acid-methanol method, etc.

In addition, separation of the fatty acids from the lipids containing the fatty acids described above can be performed by concentrating and separation in a conventional manner (e.g., the urea addition method, the cooling separation method, column chromatography, etc.) in the sate of mixed fatty acids or mixed fatty acid esters.

The lipid or fatty acid composition obtained by the production method of the present invention can be used to produce, e.g., food, pharmaceuticals, industrial materials (raw materials for cosmetics, soaps, etc.) containing oils and fats, and the like.

In a still other embodiment, the present invention provides a method for preparing foods, cosmetics, pharmaceuticals, soaps, etc. using the lipid-producing fungus transformant or yeast transformant of the present invention. The method involves the step of forming lipids or fatty acids using the lipid-producing fungus transformant or yeast transformant of the present invention. Foods, cosmetics, pharmaceuticals, soaps, etc. containing the formed lipids or fatty acids are prepared in a conventional manner. As such, the foods, cosmetics, pharmaceuticals, soaps, etc. prepared by the method of the present invention contain the lipids or fatty acids formed using the lipid-producing fungus transformant or yeast transformant of the present invention. The present invention further provides the foods, cosmetics, pharmaceuticals, soaps, etc. prepared by the method.

The form of the cosmetic (composition) or pharmaceutical (composition) of the present invention is not particularly limited and may be any form including the state of a solution, paste, gel, solid or powder. Also, the cosmetic composition or pharmaceutical composition of the present invention may be used as cosmetics or topical agents for the skin, including an oil, lotion, cream, emulsion, gel, shampoo, hair rinse, hair conditioner, enamel, foundation, lipstick, face powder, facial pack, ointment, perfume, powder, eau de cologne, tooth paste, soap, aerosol, cleansing foam, etc., an anti-aging skin care agent, anti-inflammatory agent for the skin, bath agent, medicated tonic, skin beauty essence, sun protectant, or protective and improving agent for skin troubles caused by injury, chapped or cracked skin, etc.

The cosmetic composition of the present invention may further be formulated appropriately with other oils and fats and/or dyes, fragrances, preservatives, surfactants, pigments, antioxidants, etc., if necessary. Furthermore, the pharmaceutical composition of the present invention may also contain other pharmaceutically active components (e.g., anti-inflammatory components) or aid components (e.g., lubricant or carrier components). Examples of the other components commonly used in a cosmetic or a skin preparation for external use include an agent for acne, an agent for preventing dandruff or itching, an antiperspirant and deodorant agent, an agent for burn injury, an anti-mite and lice agent, an agent for softening keratin, an agent for xeroderma, an antiviral agent, a percutaneous absorption promoting agent, and the like.

The food product of the present invention includes a dietary supplement, health food, functional food, food for young children, baby food, infant modified milk, premature infant modified milk, geriatric food, etc. As used herein, the food is intended to mean a solid, fluid and liquid food as well as a mixture thereof, and collectively means an edible stuff.

The term dietary supplement refers to food products enriched with specific nutritional ingredients. The term health food refers to food products that are healthful or good for health, and encompasses dietary supplements, natural foods and diet foods. The term functional food refers to a food product for replenishing nutritional ingredients which assist body control functions. Functional foods are synonymous with foods for specified health use. The term food for young children refers to a food product given to children up to about 6 years old. The term geriatric food refers to a food product treated to facilitate digestion and absorption when compared to untreated foods. The term infant modified milk refers to modified milk given to children up to about one year old. The term premature infant modified milk refers to modified milk given to premature infants until about 6 months after birth.

These food products include natural foods (treated with fats and oils) such as meat, fish and nuts; foods supplemented with fats and oils during preparation, e.g., Chinese foods, Chinese noodles, soups, etc.; foods prepared using fats and oils as heating media, e.g., tempura or deep-fried fish and vegetables, deep-fried foods, fried bean curd, Chinese fried rice, doughnuts, Japanese fried dough cookies or karinto; fat- and oil-based foods or processed foods supplemented with fats and oils during processing, e.g., butter, margarine, mayonnaise, dressing, chocolate, instant noodles, caramel, biscuits, cookies, cake, ice cream; and foods sprayed or coated with fats and oils upon finishing, e.g., rice crackers, hard biscuits, sweet bean paste bread, etc. However, the food product is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine or sake, medicinal liquor, sweet cooking sherry (mirin), vinegar, soy sauce and miso or bean paste, etc.; livestock food products such as yoghurt, ham, bacon, sausage, etc.; seafood products such as minced and steamed fish cake or kamaboko, deep-fried fish cake or ageten and puffy fish cake or hanpen, etc.; as well as fruit drinks, soft drinks, sports drinks, alcoholic beverages, tea, etc.

The food of the present invention may also be in the form of pharmaceutical preparations such as capsules, etc., or in the form of a processed food such as natural liquid diets, defined formula diets and elemental diets formulated with the oil and fat of the present invention together with proteins, sugars, trace elements, vitamins, emulsifiers, aroma chemicals, etc., health drinks, enteral nutrients, and the like.

As described above, fatty acids can be efficiently produced by expressing the GPAT3 gene of the present invention in host cells.

In addition, the expression level of the gene can be used as an indicator to study culture conditions, control incubation, etc. for efficient production of fatty acids.

EXAMPLES

Hereinafter, the present invention is described in more detail with reference to EXAMPLES but is not deemed to limit the scope of the invention to these EXAMPLES.

Example 1

Genome Analysis of *M. alpina*

The *M. alpina* 1S-4 strain was plated on 100 ml of GY2:1 medium (2% glucose, 1% yeast extract, pH 6.0) followed by shake culture at 28° C. for 2 days. The fungal cells were collected by filtration, and genomic DNA was prepared using DNeasy (QIAGEN).

The nucleotide sequence of the genomic DNA described above was determined using a Roche 454 Genome Sequencer FLX Standard. This case involved two runs of nucleotide sequencing of a fragment library and three runs of nucleotide sequencing of a mate paired library. The resulting nucleotide sequences were assembled into 300 supercontigs.

Synthesis of cDNA of *M. Alpina* Strain 1S-4

The *M. alpina* 1S-4 strain was plated on 4 ml of a medium (2% glucose, 1% yeast extract, pH 6.0) and cultured for 4 days at 28° C. The cells were recovered by filtration, and RNA was extracted using a RNeasy Plant Kit (QIAGEN). cDNA was synthesized using SuperScript First Strand System for RT-PCR (Invitrogen).

Search of GPAT Homologs

The amino acid sequence of MaGPAT1 (ATCC#16266) was searched against the genome nucleotide sequence of *M. alpina* 1S-4 strain using tblastn. As a result, the supercontigs containing the sequences shown in SEQ ID NO: 4 and SEQ ID NO: 5 were identified. SEQ ID NO: 5 was considered to be the genome sequence of the *M. alpina* 1S-4 strain-derived GPAT 1 (hereinafter referred to as MaGPAT 1). On the other hand, SEQ ID NO: 4 was considered to be the sequence encoding a new GPAT homolog, based on the appearance of initiation codon or termination codon and the comparison with MaGPAT1. In addition, the first to third residues and the 3278th to 3280th residues in SEQ ID NO: 4 were assumed to be the initiation codon and the termination codon of this homolog, respectively. This gene was named MaGPAT3.

Cloning of MaGPAT3 Gene

For cloning of CDS of the MaGPAT3 gene, the following primers were produced.

```
Eco-MaGPAT3-F:
                                      (SEQ ID NO: 6)
5'-GAATTCATGGGTCTCCAGATCTATGACTTCGTCTC-3'

Sal-MaGPAT3-R:
                                      (SEQ ID NO: 7)
5'-GTCGACTTATGCCTCCTTAGACTTGACTGCATCC-3'
```

Using the aforesaid cDNA as a template, PCR amplification was performed with KOD-Plus (TOYOBO) using the primers Eco-MaGPAT3-F and Sal-MaGPAT3-R, and the DNA fragment of approximately 2.2 kb was amplified. The fragment was cloned using a Zero Blunt TOPO PCR Cloning Kit (Invitrogen), and the resulting plasmid was named pCR-MAGPAT3. The insert sequence of this plasmid, i.e., the CDS sequence of MaGPAT3 gene is shown in SEQ ID NO: 3. The ORF sequence of MaGPAT3 gene is also shown in SEQ ID NO: 1.

Sequencing Analysis

From the comparison between the genome sequence (SEQ ID NO: 4) and CDS sequence (SEQ ID NO: 3) of the MaGPAT3 gene, it is assumed that the genome sequence of the gene would contain 7 exons and 6 introns and encode a protein consisting of 753 amino acid residues (FIGS. 1 and 2). The sequence of MaGPAT3 was compared with the sequence of known GPAT homologue from *M. alpina*. The CDS sequence of MaGPAT3 showed the homology of 73.7% to GPAT1 (ATCC#16266) and 73.2% to GPAT1 (1S-4). The amino acid sequence of MaGPAT3 showed the homology of 14.4% to GPAT2 (1S-4).

The putative amino acid sequence (SEQ ID NO: 2) of MaGPAT3 was submitted for homology analysis to the amino acid sequence registered at GENEBANK nr by BLASTp. As a result, the amino acid sequence with the lowest E-value for the sequence, namely, the amino acid sequence with high homology was the *Cryptococcus neoformans* var. *neoformans* JEC21-derived GPAT homologue (GENEBANK accession No. XP_569487) and the homology of the amino acid sequence was found to be 40.3%. Also, the putative amino acid sequence of MaGPAT3 showed the homology of 33.3% to the amino acid sequence Sctlp which is yeast *S.* cerevisiae-derived GPAT, and 31.5% to the amino acid sequence of Gpt2p. The amino acid sequences were compared among *M. alpina* 1S-4-derived GPAT3 and GPAT1 and *S. cerevisiae*-derived GPATs Sct1 and Gpt2 (FIG. 4). The four domains conserved in the GPAT homologs and the amino acid residues (asterisks in FIG. 4) considered to be important for the GPAT activity and the amino acid residues (crosses in FIG. 4) considered to be important for binding to glycerol-3-phosphate, in these domains were conserved also in GPAT3.

Example 2

Complementary Experiment of Yeast *S. cerevisiae* (Δsct1, Δgpt2)

In the yeast *S. cerevisiae*, SCT1 and GPT2 are known as genes responsible for the GPAT activity; it is known that simultaneous deletion of these genes results in lethality. In order to confirm if the proteins encoded by MaGPAT1 and MaGPAT3 from *M. alpina* have the GPAT activity, a complementary experiment was performed with Δsct1 and Δgpt2. Genotypes of the strains produced in this experiment are summarized in TABLE 1.

Production of GP-1 Strain

The SCT1 gene of the Δgpt2 homozygous diploid yeast (Catalog No. YSC1021-663938) in the Yeast Knockout Strain Collection (Open Biosystems) was destroyed by the following method. First, DNA was extracted from the cells of *S. cerevisiae* S288C strain using Gen Toru-Kun (for yeast) (TAKARA BIO). Using the DNA as a template, the partial sequence of SCT1 gene was amplified by PCR with KOD-Plus (TOYOBO) using the primer XbaI-Des-SCT1-F:
5'-TCTAGAATGCCTGCACCAAAACTCAC-3 (SEQ ID NO: 8) and the primer XbaI-Des-SCT1-R: 5'-TCTAGAC-CACAAGGTGATCAGGAAGA-3' (SEQ ID NO: 9). The amplified DNA fragment of approximately 1.3 kbp was cloned using a Zero Blunt TOPO PCR Cloning Kit (Invitrogen), and the resulting plasmid was named pCR-SCT1P. Subsequently, the plasmid YEp13 was digested with restriction enzymes SalI and XhoI. The resulting DNA fragment of about 2.2 kbp containing CDS of the LEU2 gene was ligated with the DNA fragment of about 4.4 kbp obtained by digesting the plasmid pCR-SCT1P with SalI, using a Ligation High (TOYOBO) to construct the plasmid with the LEU2 gene inserted in the reverse direction to the SCT1 gene, and this plasmid was named pCR-Δsct1; LEU2. pCR-Δsct1: LEU2 was digested with restriction enzyme XbaI, and the Δgpt2 homozygous diploid yeast above was transformed by the lithium acetate method. The transformants were selected for the ability to grow in SD-Leu agar medium (2% agar) (6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan and 0.6 g of uracil) per 1 L). From the cells of the transformants obtained, DNA was extracted by the method described above. Using (1) a pair of the primer SCT1outORF-F: 5'-AGTGTAGGAAGCCCGGAATT-3 (SEQ ID NO: 10) and the primer SCT1inORF-R: 5'-GCGTAGATCCAACA-GACTAC-3' (SEQ ID NO: 11) (0.5 kbp), and (2) a pair of the primer SCT1outORF-F1 and the primer LEU2 in ORF-F: 5'-TTGCCTCTTCCAAGAGCACA-3' (SEQ ID NO: 12) (1.2 kbp), PCR amplification was performed to verify the genotype, i.e., SCT1/Δsct1: LEU2, and the transformed yeast cell having this genotype was named the GP-1 strain.

Construction of MaGPAT1-D Strain and MaGPAT3-D Strain

In order to insert the GPAT genes MaGPAT1 and MaGPAT3 of *M. alpina* into the yeast chromosomes, the plasmid pUC-URA3-MAGPAT1 and the plasmid pUC-URA3-MAGPAT3 were constructed as follows.

Plasmid pUC-URA3-MAGPAT1

The multiple cloning site of plasmid pUC18 was modified to contain the HindIII site alone. The DNA fragment of about 1.2 kbp which was obtained by digesting pURA34 (WO0131000) with HindIII was inserted into the HindIII site to construct the plasmid pUC-URA3. After pYE-MAGPAT1 (WO2008156026) was digested with restriction enzyme HindIII, the end was blunted with a Blunting Kit (TAKARA BIO). The resulting DNA fragment of about 3.5 kbp was inserted into the SmaI site of plasmid pUC-URA3 to construct the plasmid with the GPAT1 gene and the URA3 gene inserted in the same direction. This plasmid was named pUC-URA3-MAGPAT1.

Plasmid pUC-URA3-MAGPAT3

The plasmid pCR-MAGPAT3 was digested with restriction enzymes EcoRI and SalI, and the resulting DNA fragment of about 2.3 kbp was inserted into the EcoRI/SalI site of the vector pYE22m (Biosci. Biotech. Biochem., 59, 1221-1228, 1995) for yeast expression to construct the plasmid pYE-MAGPAT3. Next, the plasmid pYE-MAGPAT3 was digested with restriction enzyme HindIII, and then the end was blunted with a Blunting Kit (TAKARA BIO). The resulting DNA fragment of about 3.6 kbp was inserted into the SmaI site of

TABLE 1

| strain | |
|---|---|
| YSC1021-663938 | diploid Δ gpt2:KanMX/Δ gpt2:KanMX, ura3/ura3, leu2/leu2, MET15/met15, LYS2/lys2 |
| GP-1 | diploid Δ gpt2:KanMX/Δ gpt2:KanMX, SCT1/Δ sct1:LEU2, ura3/ura3, leu2/leu2, MET15/met15, LYS2/lys2 |
| MaGPAT1-D | diploid Δ gpt2:KanMX/Δ gpt2:KanMX, SCT1/Δ sct1:LEU2, MaGPAT1-URA3/ura3, leu2/leu2, MET15/met15, LYS2/lys2 |
| MaGPAT3-D | diploid Δ gpt2:KanMX/Δ gpt2:KanMX, SCT1/Δ sct1:LEU2, MaGPAT3-URA3/ura3, leu2/leu2, MET15/met15, LYS2/lys2 |
| GP-11 | haploid Δ gpt2:KanMX, SCT1, ura3, leu2, met15, lys2 |
| GP-12 | haploid Δ gpt2:KanMX, SCT1, ura3, leu2, met15, lys2, pESC-URA3, pESC-LEU2 |
| MaGPAT1-11 | haploid Δ gpt2:KanMX, Δ sct1:LEU2, MaGPAT1-URA3, leu2, met15, lys2 |
| MaGPAT3-11 | haploid Δ gpt2:KanMX, Δ sct1:LEU2, MaGPAT3-URA3, leu2, met15. lys2 |
| GP-21 | haploid Δ gpt2:KanMX, SCT1, ura3, leu2, MET15, LYS2 |
| GP-22 | haploid Δ gpt2:KanMX, SCT1, ura3, leu2, MET15, LYS2, pESC-URA3, pESC-LEU2 |
| MaGPAT1-21 | haploid Δ gpt2:KanMX, Δ sct1:LEU2, MaGPAT1-URA3, leu2, MET15, LYS2 |
| MaGPAT3-21 | haploid Δ gpt2:KanMX, Δ sct1:LEU2, MaGPAT3-URA3, leu2, MET15, LYS2 | plasmid pUC-URA3 to construct the plasmid with the GPAT3 gene and the URA3 gene inserted in the same direction. This plasmid was named pUC-URA3-MAGPAT3.

The GP-1 strain was transformed with the plasmid pUC-URA3-MAGPAT1 and the plasmid pUC-URA3-MAGPAT3 with restriction enzyme HindIII, respectively, by the lithium acetate method. The transformants were selected for the ability to grow in SD-Ura agar medium (2% agar) (6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan and 1.8 g of leucine) per 1 L). DNA was extracted from the strains optionally selected from the transformants obtained, using Gen Toru-Kun (for yeast) (TAKARA BIO). In the transformant inserted with URA3-MAGPAT1, the genomic DNA was amplified by PCR using (3) a pair of the primer GPAT1-f1: 5'-GTCAAGAAGGAATTCAAGGAGCTCAAG-3' (SEQ ID NO: 13) and the primer GPAT1-r2: 5'-CCTGGGATGATGGACAAGAACAATG-3' (SEQ ID NO: 14) (1.1 kbp). In the transformant inserted with URA3-MAGPAT3, the genomic DNA was amplified by PCR using (4) a pair of the primer MaGPAT3-2F: 5'-TTTTGAACGCTTAAATGCTGGC-3' (SEQ ID NO: 15) and the primer MaGPAT3-3R: 5'-GGTCTTTTGAAGCTCTGCACGCGAC-3' (SEQ ID NO: 16) (1.1 kbp). The transformants in which insertion of the MaGPAT1 expression cassette or MaGPAT3 expression cassette into genome could be confirmed were named the MaGPAT1-D strain or the MaGPAT3-D strain.

Sporulation and Tetrad Analysis

The MaGPAT1-D and MaGPAT3-D strains were plated on YPD agar medium, respectively, and incubated at 30° C. for 2 days. The cells grown were plated on an agar medium for sporulation (0.5% potassium acetate, 2% agar) and incubated at 25° C. for 4 days. An appropriate amount of the sporulated cells were scraped off and suspended in 100 µl of Zymolyase solution (0.125 mg/ml Zymolyase 100T, 1M sorbitol, 40 mM potassium phosphate buffer (pH 6.8)). After incubation at room temperature for 30 minutes, a tube charged with the Zymolyase solution and the cells was transferred onto ice. After the formation of ascospores was microscopically confirmed, four ascospores were isolated on YPD agar medium by micromanipulation and incubated at 30° C. for 2 days to yield the colonies derived from the respective spores. The spore clones obtained were replicated in SD-Ura agar medium and SD-Leu agar medium. Incubation was performed at 30° C. for 3 days to examine a uracil auxotroph and a leucine auxotroph. The presence or absence of growth on each plate and the number of clones are shown in TABLE 2.

TABLE 2

| Phenotype | | | |
|---|---|---|---|
| SD-Ura | SD-Leu | MaGPAT1-D-derived | MaGPAT3-D-derived |
| ◯ | ◯ | 14 | 11 |
| ◯ | X | 14 | 9 |
| X | ◯ | 0 | 0 |
| X | X | 16 | 11 |
| Total | | 44 | 31 |

In the spore clones from both strains, the ratio of uracil prototrophic and leucine prototrophic strains:uracil prototrophic and leucine auxotrophic sztrain:uracil auxotrophic and leucine auxotrophic strain was approximately 1:1:1. Uracil auxotrophic and leucine prototrophic strain was not obtained. Next, in order to determine a genotype of the uracil prototrophic and leucine prototrophic strain and the uracil auxotrophic and leucine auxotrophic strain obtained from the MaGPAT1-D strain and the MaGPAT3-D strain, respectively, DNA was extracted from the cells in the same manner as described above, and PCR was performed using (1) a pair of the primer SCT1outORF-F and the primer SCT1inORF-R and (2) a pair of the primer SCT1outORF-F1 and the primer LEU2in ORF-F, and in the MaGPAT1-D-derived strain using (3) a pair of the primer GPAT1-f1 and the primer GPAT1-r2 and in the MaGPAT3-D-derived strain (4) a pair of the primer MaGPAT3-2F and the primer MaGPAT3-3R.

The uracil prototrophic and leucine prototrophic strains did not show any amplification by PCR with the pair of (1) but showed amplification with the pair of (2). It was therefore demonstrated that these strains were found to be Δsct1:LEU2. Also, since the pair of (3) or (4) showed amplification, it was demonstrated that MaGPAT1 or MaGPAT3 was inserted into these strains.

The foregoing results revealed that the Δgpt2 and Δsct1 strains caused lethality in S. cerevisiae but became viable by expressing the M. alpina-derived MaGPAT1 or MaGPAT3. That is, M. alpina-derived MaGPAT1 or MaGPAT3 was capable of complementation of the Δgpt2 and Δsct1 yeast strains. This suggested that the proteins encoded by M. alpina-derived MaGPAT1 and MaGPAT3 would have the GPAT activity.

On the other hand, in the uracil auxotrophic and leucine auxotrophic strains, amplification by PCR was observed with (1) but no amplification with (2), indicating that these strains were SCT1. No amplification with (3) or (4) demonstrated that M. alpina-derived MaGPAT1 or MaGPAT3 was not inserted.

Furthermore, these strains were replicated in SD-Met agar medium (2% agar) (6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 1.5 g of phenylalanine, 11.25 g of serine, 0.9 g of tyrosine, 4.5 g of valine, 6 g of threonine, 1.2 g of tryptophan, 1.8 g of leucine and 0.6 g of uracil) and in SD-Lys agar medium (2% agar) (6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.6 g of methionine, 1.5 g of phenylalanine, 11.25 g of serine, 0.9 g of tyrosine, 4.5 g of valine, 6 g of threonine, 1.2 g of tryptophan, 1.8 g of leucine and 0.6 g of uracil), per 1 L). Incubation was performed at 30° C. for 3 days to determine the methionine auxotroph and lysine auxotroph. Based on the results, GP-11 (#SC-1), MaGPAT1-11 (#3b, #4a, #8a), MaGPAT3-11 (#2d, #19a, #32a), GP-21 (#SC-2), MaGPAT1-21 (#1a, #2d, #13a) and MaGPAT3-21 (#10a, #20c, #26b) selected from the strains for the respective genotypes shown in TABLE 1 were provided for the following runs.

Fatty acid productivities of the strain with yeast-derived SCT1 only, the strain with M. alpina-derived GPAT1 only, the strain with M. alpina-derived GPAT3 only, as the GPAT gene, were compared. The GP-11 and GP-21 strains with yeast-derived SCT1 only described above are both ura3 and leu2 and thus require uracil and leucine. For complementation of the uracil and leucine auxotroph, GP-11 and GP-21 were co-transformed with plasmid pESC-URA3 and plasmid pESC-LEU2, respectively. The strains were selected as the transformants for the ability to grow in SD-Ura, Leu agar medium (2% agar) (6.7 g of yeast nitrogen base w/o amino acids (DIFCO), 20 g of glucose and 1.3 g of amino acid powders (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine and 1.2 g of tryptophan) per 1 L). The strains GP-12 (#1, 2, 3) and GP-22 (#1, #2, #3) optionally selected were provided for the subsequent runs.

Example 3

Fatty Acid Analysis of Yeast

The strains GP-12 (#1, 2, 3), MaGPAT1-11 (#3b, #4a, #8a), MaGPAT3-11 (#2d, #19a, #32a), GP-22 (#1, #2, #3), MaGPAT1-21 (#1a, #2d, #13a) and MaGPAT3-21 (#10a, #20c, #26b) obtained as described above were incubated as follows.

One platinum loop of each strain was plated on 10 ml of SD-Ura, Leu liquid medium, and shake cultured at 30° C. for 1 day. Then 100 µl of the culture obtained was plated on 10 ml of SD-Ura, Leu liquid medium, followed by shake culture at 30° C. for 2 days. The yeast culture was centrifuged to recover the cells. The cells were washed with 10 ml of sterile water and centrifuged again to recover the cells. The cells were lyophilized. The fatty acids in the cells were converted into the methyl esters by the hydrochloric acid-methanol method. The esters were extracted with hexane. After hexane was distilled off, the analysis was performed by gas chromatography. The results of fatty acid composition analysis are shown in TABLES 3 through 8.

TABLE 3 shows the cellular fatty acid composition (%) of the met15, lys2 yeast. The numerical values are expressed by mean±standard deviation (SD).

TABLE 3

| Strain | GP-12 | MaGPAT1-11 | MaGPAT3-11 |
| --- | --- | --- | --- |
| 16:0 | 20.54 ± 0.12 | 20.72 ± 4.77 | 29.32 ± 0.80 |
| 16:1 | 37.35 ± 0.18 | 34.02 ± 3.81 | 27.87 ± 0.64 |
| 18:0 | 6.54 ± 0.10 | 10.72 ± 1.55 | 13.42 ± 0.45 |
| 18:1 | 25.62 ± 0.17 | 24.75 ± 2.44 | 20.97 ± 0.53 |
| 18:1(n-7) | 2.99 ± 0.06 | 2.43 ± 1.32 | 0.59 ± 0.51 |
| others | 6.96 ± 0.02 | 7.36 ± 1.27 | 7.83 ± 0.26 |

TABLE 4 shows the cell density of the met15, lys2 yeast after incubation. The numerical values are expressed by mean±SD.

TABLE 4

| Strain | GP-12 | MaGPAT1-11 | MaGPAT3-11 |
| --- | --- | --- | --- |
| Cell Density (g/L) | 0.84 ± 0.03 | 0.90 ± 0.03 | 0.92 ± 0.03 |

TABLE 5 shows the fatty acid production level of the met15, lys2 yeast. The numerical values are expressed by mean±SD.

TABLE 5

| Strain | GP-12 | MaGPAT1-11 | MaGPAT3-11 |
| --- | --- | --- | --- |
| total FA (mg/L) | 42.41 ± 1.91 | 65.79 ± 24.31 | 93.76 ± 9.80 |

TABLE 6 shows the cell fatty acid composition (%) of the MET15,LYS2 yeast. The numerical values are expressed by mean±SD.

TABLE 6

| Strain | GP-22 | MaGPAT1-21 | MaGPAT3-21 |
| --- | --- | --- | --- |
| 16:0 | 7.73 ± 0.69 | 4.47 ± 0.23 | 5.88 ± 0.53 |
| 16:1 | 51.71 ± 0.64 | 51.11 ± 0.36 | 50.63 ± 0.96 |
| 18:0 | 3.54 ± 0.08 | 2.60 ± 0.02 | 3.08 ± 0.13 |
| 18:1 | 31.09 ± 0.87 | 34.11 ± 0.60 | 33.62 ± 0.73 |
| 18:1(n-7) | 3.44 ± 0.43 | 6.35 ± 0.24 | 4.58 ± 0.50 |
| other | 2.49 ± 0.40 | 1.37 ± 0.15 | 2.22 ± 0.26 |

TABLE 7 shows the cell density of the MET15,LYS2 yeast after incubation. The numerical values are expressed by mean±SD.

TABLE 7

| Strain | GP-22 | MaGPAT1-21 | MaGPAT3-21 |
| --- | --- | --- | --- |
| Cell Density (g/L) | 4.88 ± 0.22 | 4.93 ± 0.21 | 4.84 ± 0.22 |

TABLE 8 shows the fatty acid production level of the MET15,LYS2 yeast. The numerical values are expressed by mean±SD.

TABLE 8

| Strain | GP-22 | MaGPAT1-21 | MaGPAT3-21 |
| --- | --- | --- | --- |
| total FA (mg/L) | 109.09 ± 14.99 | 99.96 ± 6.71 | 121.85 ± 13.92 |

In the respective cells, the cell density was auxotrophy-dependent. The cell density of the MET 15,LYS2 yeast was higher by about 5 times than the cell density of the met15,lys2 yeast, but any influence of the GPAT gene on its fatty acid composition was not observed (TABLES 3 and 6). Further in the MET15,LYS2 yeast, any marked difference was not noted either in the fatty acid productivity based on differences in the GPAT gene.

On the other hand, in the met15,lys2 yeast, the fatty acid production level was higher by about 1.5 times in the MaGPAT 1-11 strain and higher by about 2.2 times in the MaGPAT3-11 strain, with *M. alpina*-derived GPAT gene, as compared with the GP-12 strain having only SCT1 as the GPAT gene. Furthermore, the fatty acid production level of the MaGPAT3-11 strain was higher by about 1.4 times than the MaGPAT 1-11 strain. The met15,lys2 yeast suppressed proliferation as compared with the MET15,LYS2 yeast, and it was found that expression of the *M. alpina*-derived GPAT1 gene or GPAT3 gene markedly improved the productivity of fatty acids (TABLES 4 and 5). Comparison in fatty acid composition revealed an increased ratio of saturated fatty acid palmitic acid (16:0) or stearic acid (18:0) in the MaGPAT3-11 strain, as compared with G-12 and MaGPAT1-11 strains (TABLE 3).

Example 4

Analysis of Yeast Lipids

The level of each lipid and fatty acid composition were examined for the met15,lys2 yeast GP-12 (#1, 2, 3), MaGPAT1-11 (#3b, #4a, #8a) and MaGPAT3-11 (#2d, #19a, #32a) which showed differences in the fatty acid production level.

One platinum loop of each strain was plated on 10 ml of SD-Ura, Leu liquid medium, and shake cultured at 30° C. for 1 day. Then 1 ml of the culture obtained was plated on 10 ml of SD-Ura, Leu liquid medium with 2 strains each, followed by shake culture at 30° C. for 1 day. The yeast culture was centrifuged to recover the cells. The cells were washed with 10 ml of sterile water and centrifuged again to recover the cells. The cells were lyophilized. The fatty acids in the cells per one strain were converted into the methyl esters by the hydrochloric acid-methanol method. The esters were extracted with hexane. After hexane was removed by distillation, the analysis was performed by gas chromatography.

In addition, the lipids were extracted from each one of the strains as follows. That is, 1 ml of chloroform:methanol (2:1) and glass beads were added, and the cells were disrupted by a bead beater and centrifuged to recover the supernatant. To the remaining cells was further added 1 ml chloroform:methanol (2:1), and the supernatant was recovered as above, which was repeated to recover the lipids with total 4 ml of chloroform:methanol (2:1). The solvent was removed by distillation using a speed-vac and the residue was dissolved in a small quantity of chloroform. Thin layer chromatography was performed under the conditions of Silica Gel 60 Plate (Merck) and developing solvent, hexane:diethyl ether:acetic acid=70:30:1 to fractionate the lipids. The lipids were detected by spraying a primulin solution and irradiating with UV rays. The triglyceride fraction and the phospholipid fraction were scraped off, respectively, and collected in test tubes. The fatty acids were converted into the methyl esters by the hydrochloric acid-methanol method. The analysis of fatty acids was performed by gas chromatography.

The results are shown in TABLES below.

TABLE 9

Cell Density After Incubation of met15, lys2 Yeast (mean + SD)

| Strain | GP-12 | MaGPAT1-11 | MaGPAT3-11 |
|---|---|---|---|
| (g/L) | 9.40 ± 0.53 | 9.37 ± 0.64 | 9.53 ± 0.45 |

TABLE 10

Total Fatty Acid Level of met15, lys2 Yeast (mean + SD)

| Strain | GP-12 | MaGPAT1-11 | MaGPAT3-11 |
|---|---|---|---|
| (mg/L) | 40.55 ± 2.34 | 60.74 ± 4.99 | 86.53 ± 0.53 |

TABLE 11

Fatty Acid Level in Phospholipid Fraction of met15, lys2 Yeast (mean + SD)

| Strain | GP-12 | MaGPAT1-11 | MaGPAT3-11 |
|---|---|---|---|
| (mg/L) | 10.73 ± 4.91 | 10.16 ± 0.84 | 11.22 ± 3.01 |

TABLE 12

Fatty Acid Composition in Phospholipid Fraction of met15, lys2 Yeast (%) (mean + SD)

| Strain | GP-12 | MaGPAT1-11 | MaGPAT3-11 |
|---|---|---|---|
| 16:0 | 27.08 ± 1.54 | 25.24 ± 2.29 | 28.18 ± 1.52 |
| 16:1 | 31.33 ± 4.71 | 32.82 ± 0.82 | 31.97 ± 1.69 |
| 18:0 | 8.63 ± 4.38 | 9.89 ± 0.59 | 9.56 ± 2.76 |

TABLE 12-continued

Fatty Acid Composition in Phospholipid Fraction of met15, lys2 Yeast (%) (mean + SD)

| Strain | GP-12 | MaGPAT1-11 | MaGPAT3-11 |
|---|---|---|---|
| 18:1 | 27.44 ± 6.06 | 28.12 ± 1.78 | 26.97 ± 3.24 |
| other | 5.53 ± 4.86 | 3.94 ± 1.55 | 3.31 ± 0.57 |

TABLE 13

Fatty Acid Level in Triglyceride Fraction of met15, lys2 Yeast (%) (mean + SD)

| Strain | GP-12 | MaGPAT1-11 | MaGPAT3-11 |
|---|---|---|---|
| (mg/L) | 17.18 ± 0.16 | 27.43 ± 4.23 | 35.32 ± 3.97 |

TABLE 14

Fatty Acid Composition in Triglyceride Fraction of met15, lys2 Yeast (%) (mean + SD)

| Strain | GP-12 | MaGPAT1-11 | MaGPAT3-11 |
|---|---|---|---|
| 16:0 | 19.88 ± 0.46 | 20.72 ± 4.19 | 27.39 ± 0.70 |
| 16:1 | 38.61 ± 1.15 | 33.90 ± 3.12 | 29.34 ± 0.69 |
| 18:0 | 7.10 ± 1.32 | 11.16 ± 1.05 | 12.76 ± 0.33 |
| 18:1 | 24.96 ± 0.88 | 24.53 ± 3.18 | 20.34 ± 0.48 |
| other | 9.44 ± 0.45 | 9.70 ± 1.06 | 10.17 ± 0.25 |

The cell density was not affected by the GPAT genes. In the fatty acid production level per medium, the MaGPAT 1-11 strain with *Mortierella alpina*-derived the GPAT gene showed higher by about 1.5 times and the MaGPAT3-11 strain higher by about 2 times, than the GP-12 strain having only SCT1 as the GPAT gene.

The fatty acid level and fatty acid composition of phospholipids were not affected by the GPAT genes. On the other hand, the triglyceride level was higher by about 1.6 times in the MaGPAT1-11 strain and higher by about 2 times in the MaGPAT3-11 strain, with *Mortierella alpina*-derived GPAT gene, than the GP-12 strain having only SCT1 as the GPAT gene.

It was found that the increased total fatty acid production level in the MaGPAT 1-11 strain and the MaGPAT3-11 strain was mainly due to the increased triglyceride level. Comparison of the fatty acid composition in the triglycerides revealed an increased ratio of saturated fatty acids in the MaGPAT3-11 strain, as compared with the GP-12 strain.

It was found that the productivity of triglycerides in particular could be improved by expressing the MaGPAT3 gene.

INDUSTRIAL APPLICABILITY

By expressing the polynucleotide of the present invention in an appropriate host cell, triglycerides can be efficiently produced irrespective of growth rate of the host cell. Furthermore, increased triglycerides result in increasing fatty acids as well, which form triglycerides. According to the present invention, the triglycerides and fatty acids can be used to produce foods, cosmetics, pharmaceuticals, soaps, and so on.

The invention claimed is:

1. A cDNA comprising any one of (a) to (d) below:
    (a) the nucleotide sequence of SEQ ID NO: 1 or 4;
    (b) a polynucleotide encoding the amino acid sequence of SEQ ID NO: 2;
    (c) a polynucleotide encoding an amino acid sequence wherein 1 to 37 amino acids are deleted, substituted, inserted and/or added in the amino acid sequence of SEQ ID NO: 2, and having a glycerol-3-phosphate acyltransferase activity;
    (d) a polynucleotide encoding a protein having an amino acid sequence having at least 95% homology to the amino acid sequence of SEQ ID NO: 2 and a glycerol-3-phosphate acyltransferase activity.

2. The cDNA according to claim 1 comprising:
a polynucleotide encoding an amino acid sequence wherein 1 to 10 amino acids are deleted, substituted, inserted and/or added in the amino acid sequence of SEQ ID NO: 2, and having a glycerol-3-phosphate acyltransferase activity; or
a polynucleotide encoding a protein having an amino acid sequence having at least 98% homology to the amino acid sequence of SEQ ID NO: 2 and a glycerol-3-phosphate acyltransferase activity.

3. The cDNA according to claim 1, comprising the nucleotide sequence of SEQ ID NO: 1 or 4.

4. The cDNA according to claim 1, encoding the amino acid sequence of SEQ ID NO: 2.

5. A non-human transformant introduced with the cDNA according to claim 1.

6. The transformant according to claim 5, wherein the transformant is a lipid-producing fungus.

7. The transformant according to claim 6, wherein the lipid-producing fungus is *Mortierella alpina*.

8. A method for producing a lipid or fatty acid composition, which comprises collecting the lipid or fatty acid composition from a culture of the transformant according to claim 5.

9. The cDNA according to claim 1 comprising:
the nucleotide sequence of SEQ ID NO: 1 or 4;
a polynucleotide encoding the amino acid sequence of SEQ ID NO: 2; or
a polynucleotide encoding a protein having an amino acid sequence having at least 98% homology to the amino acid sequence of SEQ ID NO: 2 and a glycerol-3-phosphate acyltransferase activity.

10. A recombinant vector comprising any one of (a) to (d) below:
(a) the nucleotide sequence of SEQ ID NO: 1 or 4;
(b) a polynucleotide encoding the amino acid sequence of SEQ ID NO: 2;
(c) a polynucleotide encoding an amino acid sequence wherein 1 to 37 amino acids are deleted, substituted, inserted and/or added in the amino acid sequence of SEQ ID NO: 2, and having a glycerol-3-phosphate acyltransferase activity;
(d) a polynucleotide encoding a protein having an amino acid sequence having at least 95% homology to the amino acid sequence of SEQ ID NO: 2 and a glycerol-3-phosphate acyltransferase activity.

11. The recombinant vector according to claim 10 comprising:
a polynucleotide encoding an amino acid sequence wherein 1 to 10 amino acids are deleted, substituted, inserted and/or added in the amino acid sequence of SEQ ID NO: 2, and having a glycerol-3-phosphate acyltransferase activity; or
a polynucleotide encoding an amino acid sequence having at least 98% homology to the amino acid sequence of SEQ ID NO: 2 and a glycerol-3-phosphate acyltransferase activity.

12. The recombinant vector according to claim 10, comprising the nucleotide sequence of SEQ ID NO: 1 or 4.

13. The recombinant vector according to claim 10, encoding the amino acid sequence of SEQ ID NO: 2.

14. A non-human transformant introduced with the recombinant vector according to claim 10.

15. The transformant according to claim 14, wherein the transformant is a lipid-producing fungus.

16. The transformant according to claim 15, wherein the lipid-producing fungus is *Mortierella alpina*.

* * * * *

SEQUENCE LISTING

<160> NUMBER OF SEQ ID NOS: 20

<210> SEQ ID NO 1
<211> LENGTH: 2259
<212> TYPE: DNA
<213> ORGANISM: Mortierella alpina

<400> SEQUENCE: 1

```
atgggtctcc agatctatga cttcgtctca ttcttcttca ccctcctgct cgacatcttc      60
ttcagggaaa tccgtcctcg gggggcccac aagatccccc gacaaggacc cgtcattttt     120
gtcgccgccc ctcatgccaa tcagtttgtt gatccactcg tgttgatgcg cgaatgtggc     180
cgacgagtct cgttcctggc tgccaaaaag tcaatggacc gtcgctggat aggcgccatg     240
gcgcgttcca tgaatgccat tcctgtggag cgtcctcagg acttggctaa ggctggttcg     300
ggaacgatca aactggtgga tcgctatggc gaccctctcc gcatcactgg gctcggtacc     360
aaattcacaa aggaactctt tgtcggcgac cagatttcgc tcccaaagga cgttggaacc     420
tcggctgtgg tcgagatcat ctcggacact gaactgattg tcaagaaaga gttcaaggag     480
ctcaaggcac tggagctttt aaccagtgct gagggatcca agtacaagtg catgcctcac     540
atggaccaga gcaaggtcta caagactgtt tttgaacgct aaatgctggc cattgtgtt      600 ggcatctttc ctgaaggagg ttcacacgat cgtgcagaga tgctgcccct gaaagctggt     660
gtcaccatca tggcgcttgg cgcactggcc gctaaccctg acctggacct taaaattgtg     720
acctgcggcc tgaactattt ccacccccat cgattccgtt ctcgcgccgt tgttgagttt     780
ggtgagcctt tgaccgtgcc tccagaactt gtcgagatgt acaagagggg tggagctgag     840
aagcgcgagg cctgcggaaa gctcctcgac accatctacg atgcactcaa gaatgtcaca     900
ctgaacgccc ccgattacga aacactcatg gttattcaag ctgcccgccg tctctacaag     960
ccaacacatc gcaagctgca gatctctcaa gttgtggagt tgaaccgtcg cttcgtcgct    1020
ggttatctgc actttcagga caacccaaag gtgattgata caaaggacaa agttatgcac    1080
tacaacactc agctacgcta tcatggactt cgcgaccacc aggtcaacat ccgcacaact    1140
cggcgacatg ccattgaact attgattttgg cgagttgtgc agatggtctt tttgagtcta    1200
ctagcgcttc caggtaccat gatgaatctt ccagttgcca tcgttgctcg catcatcagc    1260
aacaagaagg ccaaggaggc tttggctgca tcgaccgtga aaattgcagg aagggacgtt    1320
ctagccacat ggaagttgct tgtggccctg ggattgatgc ccgtcctttta cttttcgtac    1380 tcgtttgtta tcttttttgct gtgtggacgg ttcgacatta cgctcaagac ccgcctcctg    1440
atcgcttggg cggcttgggc ctgcattccg tttgtgacct acgccagtat ccgtttcggt    1500
gaggtgggta tcgatatctt caagtcgatc cgtcctctct tcttgtcaat cattcccggc    1560
gaggaaaaca cgatcaatga gctccgcaag tcgcgtgcag agcttcaaaa gaccatcaac    1620
gagctcatca atgagctggc gccggaaata taccccgact tgattccaa acgaatcttg     1680 gacccttcgc caaacgatcg acccagccgc ggcgcgtcgc gctccgcctc gggcaccaac    1740
cttgcgcaga ccattttcaa caccatgaac acggccacac agccgctaaa ccaatggctc    1800
ggtatggatg gcgcttcga gtgggagcgt gtggacgact cggatgcgga cgacgtgttc     1860
tttttcctca accctgcagg agccatccaa gggcgatcga ggacgtcttc ttggggtgct    1920
ggagcatgga cgccttcgtc tgctggcgat ggttctcggt ctcggtcaag gagtcgcagt    1980
cggacgagct cgtttgcgtc agggcagatt cagctgggcg aagggttcaa gctggaggca    2040
ttgacagagc tgccaaagga taagcctttt ggcgaggtga cacgacgact cagcttgagt    2100
```

```
cgcaagcaga agcatggact ggtgggcgac atgaccaagg atcccgagga gattgagaag    2160
cagggcggat ttatgcatga gggacacttt gtcagcacac cgcccatcac ggttcagaac    2220
atggatgatc ctatggatgc agtcaagtct aaggaggca                           2259

<210> SEQ ID NO 2
<211> LENGTH: 753
<212> TYPE: PRT
<213> ORGANISM: Mortierella alpina

<400> SEQUENCE: 2

Met Gly Leu Gln Ile Tyr Asp Phe Val Ser Phe Phe Thr Leu Leu
1               5                   10                  15

Leu Asp Ile Phe Phe Arg Glu Ile Arg Pro Arg Gly Ala His Lys Ile
            20                  25                  30

Pro Arg Gln Gly Pro Val Ile Phe Val Ala Ala Pro His Ala Asn Gln
        35                  40                  45

Phe Val Asp Pro Leu Val Leu Met Arg Glu Cys Gly Arg Arg Val Ser
    50                  55                  60

Phe Leu Ala Ala Lys Lys Ser Met Asp Arg Arg Trp Ile Gly Ala Met
65                  70                  75                  80

Ala Arg Ser Met Asn Ala Ile Pro Val Glu Arg Pro Gln Asp Leu Ala
                85                  90                  95

Lys Ala Gly Ser Gly Thr Ile Lys Leu Val Asp Arg Tyr Gly Asp Pro
            100                 105                 110

Leu Arg Ile Thr Gly Leu Gly Thr Lys Phe Thr Lys Glu Leu Phe Val
        115                 120                 125

Gly Asp Gln Ile Ser Leu Pro Lys Asp Val Gly Thr Ser Ala Val Val
    130                 135                 140

Glu Ile Ile Ser Asp Thr Glu Leu Ile Val Lys Lys Glu Phe Lys Glu
145                 150                 155                 160

Leu Lys Ala Leu Glu Leu Leu Thr Ser Ala Glu Gly Ser Lys Tyr Lys
                165                 170                 175

Cys Met Pro His Met Asp Gln Ser Lys Val Tyr Lys Thr Val Phe Glu
            180                 185                 190

Arg Leu Asn Ala Gly His Cys Val Gly Ile Phe Pro Glu Gly Gly Ser
        195                 200                 205

His Asp Arg Ala Glu Met Leu Pro Leu Lys Ala Gly Val Thr Ile Met
    210                 215                 220

Ala Leu Gly Ala Leu Ala Ala Asn Pro Asp Leu Asp Leu Lys Ile Val
225                 230                 235                 240

Thr Cys Gly Leu Asn Tyr Phe His Pro His Arg Phe Arg Ser Arg Ala
                245                 250                 255

Val Val Glu Phe Gly Glu Pro Leu Thr Val Pro Pro Glu Val Glu
            260                 265                 270

Met Tyr Lys Arg Gly Gly Ala Glu Lys Arg Glu Ala Cys Gly Lys Leu
        275                 280                 285

Leu Asp Thr Ile Tyr Asp Ala Leu Lys Asn Val Thr Leu Asn Ala Pro
    290                 295                 300

Asp Tyr Glu Thr Leu Met Val Ile Gln Ala Ala Arg Arg Leu Tyr Lys
305                 310                 315                 320

Pro Thr His Arg Lys Leu Gln Ile Ser Gln Val Val Glu Leu Asn Arg
                325                 330                 335

Arg Phe Val Ala Gly Tyr Leu His Phe Gln Asp Asn Pro Lys Val Ile
            340                 345                 350
```

-continued

```
Asp Thr Lys Asp Lys Val Met His Tyr Asn Thr Gln Leu Arg Tyr His
            355                 360                 365
Gly Leu Arg Asp His Gln Val Asn Ile Arg Thr Thr Arg Arg His Ala
370                 375                 380
Ile Glu Leu Leu Ile Trp Arg Val Val Gln Met Val Phe Leu Ser Leu
385                 390                 395                 400
Leu Ala Leu Pro Gly Thr Met Met Asn Leu Pro Val Ala Ile Val Ala
                405                 410                 415
Arg Ile Ile Ser Asn Lys Lys Ala Lys Glu Ala Leu Ala Ala Ser Thr
                420                 425                 430
Val Lys Ile Ala Gly Arg Asp Val Leu Ala Thr Trp Lys Leu Leu Val
            435                 440                 445
Ala Leu Gly Leu Met Pro Val Leu Tyr Phe Ser Tyr Ser Phe Val Ile
            450                 455                 460
Phe Leu Leu Cys Gly Arg Phe Asp Ile Thr Leu Lys Thr Arg Leu Leu
465                 470                 475                 480
Ile Ala Trp Ala Ala Trp Ala Cys Ile Pro Phe Val Thr Tyr Ala Ser
                485                 490                 495
Ile Arg Phe Gly Glu Val Gly Ile Asp Ile Phe Lys Ser Ile Arg Pro
                500                 505                 510
Leu Phe Leu Ser Ile Ile Pro Gly Glu Glu Asn Thr Ile Asn Glu Leu
            515                 520                 525
Arg Lys Ser Arg Ala Glu Leu Gln Lys Thr Ile Asn Glu Leu Ile Asn
            530                 535                 540
Glu Leu Ala Pro Glu Ile Tyr Pro Asp Phe Asp Ser Lys Arg Ile Leu
545                 550                 555                 560
Asp Pro Ser Pro Asn Asp Arg Pro Ser Arg Gly Ala Ser Arg Ser Ala
                565                 570                 575
Ser Gly Thr Asn Leu Ala Gln Thr Ile Phe Asn Thr Met Asn Thr Ala
                580                 585                 590
Thr Gln Pro Leu Asn Gln Trp Leu Gly Met Asp Gly Arg Phe Glu Trp
            595                 600                 605
Glu Arg Val Asp Asp Ser Asp Ala Asp Val Phe Phe Leu Asn
            610                 615                 620
Pro Ala Gly Ala Ile Gln Gly Arg Ser Arg Thr Ser Ser Trp Gly Ala
625                 630                 635                 640
Gly Ala Trp Thr Pro Ser Ser Ala Gly Asp Gly Ser Arg Ser Arg Ser
                645                 650                 655
Arg Ser Arg Ser Arg Thr Ser Ser Phe Ala Ser Gly Gln Ile Gln Leu
                660                 665                 670
Gly Glu Gly Phe Lys Leu Glu Ala Leu Thr Glu Leu Pro Lys Asp Lys
            675                 680                 685
Pro Phe Gly Glu Val Thr Arg Arg Leu Ser Leu Ser Lys Gln Lys
690                 695                 700
His Gly Leu Val Gly Asp Met Thr Lys Asp Pro Glu Glu Ile Glu Lys
705                 710                 715                 720
Gln Gly Gly Phe Met His Glu Gly His Phe Val Ser Thr Pro Pro Ile
                725                 730                 735
Thr Val Gln Asn Met Asp Asp Pro Met Asp Ala Val Lys Ser Lys Glu
            740                 745                 750
Ala
```

-continued

```
<210> SEQ ID NO 3
<211> LENGTH: 2262
<212> TYPE: DNA
<213> ORGANISM: Mortierella alpina
<220> FEATURE:
<221> NAME/KEY: CDS
<222> LOCATION: (1)..(2259)

<400> SEQUENCE: 3
```

| | | | | | | | | | | | | | | | | |
|---|---|---|---|---|---|---|---|---|---|---|---|---|---|---|---|---|
| atg | ggt | ctc | cag | atc | tat | gac | ttc | gtc | tca | ttc | ttc | ttc | acc | ctc | ctg | 48 |
| Met | Gly | Leu | Gln | Ile | Tyr | Asp | Phe | Val | Ser | Phe | Phe | Phe | Thr | Leu | Leu | |
| 1 | | | | 5 | | | | | 10 | | | | | 15 | | |
| ctc | gac | atc | ttc | ttc | agg | gaa | atc | cgt | cct | cgg | ggg | gcc | cac | aag | atc | 96 |
| Leu | Asp | Ile | Phe | Phe | Arg | Glu | Ile | Arg | Pro | Arg | Gly | Ala | His | Lys | Ile | |
| | | | 20 | | | | | 25 | | | | | 30 | | | |
| ccc | cga | caa | gga | ccc | gtc | att | ttt | gtc | gcc | gcc | cct | cat | gcc | aat | cag | 144 |
| Pro | Arg | Gln | Gly | Pro | Val | Ile | Phe | Val | Ala | Ala | Pro | His | Ala | Asn | Gln | |
| | 35 | | | | | 40 | | | | | 45 | | | | | |
| ttt | gtt | gat | cca | ctc | gtg | ttg | atg | cgc | gaa | tgt | ggc | cga | cga | gtc | tcg | 192 |
| Phe | Val | Asp | Pro | Leu | Val | Leu | Met | Arg | Glu | Cys | Gly | Arg | Arg | Val | Ser | |
| 50 | | | | | 55 | | | | | 60 | | | | | | |
| ttc | ctg | gct | gcc | aaa | aag | tca | atg | gac | cgt | cgc | tgg | ata | ggc | gcc | atg | 240 |
| Phe | Leu | Ala | Ala | Lys | Lys | Ser | Met | Asp | Arg | Arg | Trp | Ile | Gly | Ala | Met | |
| 65 | | | | 70 | | | | | 75 | | | | | 80 | | |
| gcg | cgt | tcc | atg | aat | gcc | att | cct | gtg | gag | cgt | cct | cag | gac | ttg | gct | 288 |
| Ala | Arg | Ser | Met | Asn | Ala | Ile | Pro | Val | Glu | Arg | Pro | Gln | Asp | Leu | Ala | |
| | | | | 85 | | | | | 90 | | | | | 95 | | |
| aag | gct | ggt | tcg | gga | acg | atc | aaa | ctg | gtg | gat | cgc | tat | ggc | gac | cct | 336 |
| Lys | Ala | Gly | Ser | Gly | Thr | Ile | Lys | Leu | Val | Asp | Arg | Tyr | Gly | Asp | Pro | |
| | | | 100 | | | | | 105 | | | | | 110 | | | |
| ctc | cgc | atc | act | ggg | ctc | ggt | acc | aaa | ttc | aca | aag | gaa | ctc | ttt | gtc | 384 |
| Leu | Arg | Ile | Thr | Gly | Leu | Gly | Thr | Lys | Phe | Thr | Lys | Glu | Leu | Phe | Val | |
| | | 115 | | | | | 120 | | | | | 125 | | | | |
| ggc | gac | cag | att | tcg | ctc | cca | aag | gac | gtt | gga | acc | tcg | gct | gtg | gtc | 432 |
| Gly | Asp | Gln | Ile | Ser | Leu | Pro | Lys | Asp | Val | Gly | Thr | Ser | Ala | Val | Val | |
| | 130 | | | | | 135 | | | | | 140 | | | | | |
| gag | atc | atc | tcg | gac | act | gaa | ctg | att | gtc | aag | aaa | gag | ttc | aag | gag | 480 |
| Glu | Ile | Ile | Ser | Asp | Thr | Glu | Leu | Ile | Val | Lys | Lys | Glu | Phe | Lys | Glu | |
| 145 | | | | | 150 | | | | | 155 | | | | | 160 | |
| ctc | aag | gca | ctg | gag | ctt | tta | acc | agt | gct | gag | gga | tcc | aag | tac | aag | 528 |
| Leu | Lys | Ala | Leu | Glu | Leu | Leu | Thr | Ser | Ala | Glu | Gly | Ser | Lys | Tyr | Lys | |
| | | | | 165 | | | | | 170 | | | | | 175 | | |
| tgc | atg | cct | cac | atg | gac | cag | agc | aag | gtc | tac | aag | act | gtt | ttt | gaa | 576 |
| Cys | Met | Pro | His | Met | Asp | Gln | Ser | Lys | Val | Tyr | Lys | Thr | Val | Phe | Glu | |
| | | | | 180 | | | | | 185 | | | | | 190 | | |
| cgc | tta | aat | gct | ggc | cat | tgt | gtt | ggc | atc | ttt | cct | gaa | gga | ggt | tca | 624 |
| Arg | Leu | Asn | Ala | Gly | His | Cys | Val | Gly | Ile | Phe | Pro | Glu | Gly | Gly | Ser | |
| | | | 195 | | | | | 200 | | | | | 205 | | | |
| cac | gat | cgt | gca | gag | atg | ctg | ccc | ctg | aaa | gct | ggt | gtc | acc | atc | atg | 672 |
| His | Asp | Arg | Ala | Glu | Met | Leu | Pro | Leu | Lys | Ala | Gly | Val | Thr | Ile | Met | |
| | 210 | | | | | 215 | | | | | 220 | | | | | |
| gcg | ctt | ggc | gca | ctg | gcc | gct | aac | cct | gac | ctg | gac | ctt | aaa | att | gtg | 720 |
| Ala | Leu | Gly | Ala | Leu | Ala | Ala | Asn | Pro | Asp | Leu | Asp | Leu | Lys | Ile | Val | |
| 225 | | | | | 230 | | | | | 235 | | | | | 240 | |
| acc | tgc | ggc | ctg | aac | tat | ttc | cac | ccc | cat | cga | ttc | cgt | tct | cgc | gcc | 768 |
| Thr | Cys | Gly | Leu | Asn | Tyr | Phe | His | Pro | His | Arg | Phe | Arg | Ser | Arg | Ala | |
| | | | | 245 | | | | | 250 | | | | | 255 | | |
| gtt | gtt | gag | ttt | ggt | gag | cct | ttg | acc | gtg | cct | cca | gaa | ctt | gtc | gag | 816 |
| Val | Val | Glu | Phe | Gly | Glu | Pro | Leu | Thr | Val | Pro | Pro | Glu | Leu | Val | Glu | |
| | | | | 260 | | | | | 265 | | | | | 270 | | |

```
atg tac aag agg ggt gga gct gag aag cgc gag gcc tgc gga aag ctc      864
Met Tyr Lys Arg Gly Gly Ala Glu Lys Arg Glu Ala Cys Gly Lys Leu
        275                 280                 285 ctc gac acc atc tac gat gca ctc aag aat gtc aca ctg aac gcc ccc      912
Leu Asp Thr Ile Tyr Asp Ala Leu Lys Asn Val Thr Leu Asn Ala Pro
290                 295                 300 gat tac gaa aca ctc atg gtt att caa gct gcc cgc cgt ctc tac aag      960
Asp Tyr Glu Thr Leu Met Val Ile Gln Ala Ala Arg Arg Leu Tyr Lys
305                 310                 315                 320 cca aca cat cgc aag ctg cag atc tct caa gtt gtg gag ttg aac cgt     1008
Pro Thr His Arg Lys Leu Gln Ile Ser Gln Val Val Glu Leu Asn Arg
                325                 330                 335 cgc ttc gtc gct ggt tat ctg cac ttt cag gac aac cca aag gtg att     1056
Arg Phe Val Ala Gly Tyr Leu His Phe Gln Asp Asn Pro Lys Val Ile
            340                 345                 350 gat aca aag gac aaa gtt atg cac tac aac act cag cta cgc tat cat     1104
Asp Thr Lys Asp Lys Val Met His Tyr Asn Thr Gln Leu Arg Tyr His
        355                 360                 365 gga ctt cgc gac cac cag gtc aac atc cgc aca act cgg cga cat gcc     1152
Gly Leu Arg Asp His Gln Val Asn Ile Arg Thr Thr Arg Arg His Ala
370                 375                 380 att gaa cta ttg att tgg cga gtt gtg cag atg gtc ttt ttg agt cta     1200
Ile Glu Leu Leu Ile Trp Arg Val Val Gln Met Val Phe Leu Ser Leu
385                 390                 395                 400 cta gcg ctt cca ggt acc atg atg aat ctt cca gtt gcc atc gtt gct     1248
Leu Ala Leu Pro Gly Thr Met Met Asn Leu Pro Val Ala Ile Val Ala
                405                 410                 415 cgc atc atc agc aac aag aag gcc aag gag gct ttg gct gca tcg acc     1296
Arg Ile Ile Ser Asn Lys Lys Ala Lys Glu Ala Leu Ala Ala Ser Thr
            420                 425                 430 gtg aaa att gca gga agg gac gtt cta gcc aca tgg aag ttg ctt gtg     1344
Val Lys Ile Ala Gly Arg Asp Val Leu Ala Thr Trp Lys Leu Leu Val
        435                 440                 445 gcc ctg gga ttg atg ccc gtc ctt tac ttt tcg tac tcg ttt gtt atc     1392
Ala Leu Gly Leu Met Pro Val Leu Tyr Phe Ser Tyr Ser Phe Val Ile
450                 455                 460 ttt ttg ctg tgt gga cgg ttc gac att acg ctc aag acc cgc ctc ctg     1440
Phe Leu Leu Cys Gly Arg Phe Asp Ile Thr Leu Lys Thr Arg Leu Leu
465                 470                 475                 480 atc gct tgg gcg gct tgg gcc tgc att ccg ttt gtg acc tac gcc agt     1488
Ile Ala Trp Ala Ala Trp Ala Cys Ile Pro Phe Val Thr Tyr Ala Ser
                485                 490                 495 atc cgt ttc ggt gag gtg ggt atc gat atc ttc aag tcg atc cgt cct     1536
Ile Arg Phe Gly Glu Val Gly Ile Asp Ile Phe Lys Ser Ile Arg Pro
            500                 505                 510 ctc ttc ttg tca atc att ccc ggc gag gaa aac acg atc aat gag ctc     1584
Leu Phe Leu Ser Ile Ile Pro Gly Glu Glu Asn Thr Ile Asn Glu Leu
        515                 520                 525 cgc aag tcg cgt gca gag ctt caa aag acc atc aac gag ctc atc aat     1632
Arg Lys Ser Arg Ala Glu Leu Gln Lys Thr Ile Asn Glu Leu Ile Asn
530                 535                 540 gag ctg gcg ccg gaa ata tac ccc gac ttt gat tcc aaa cga atc ttg     1680
Glu Leu Ala Pro Glu Ile Tyr Pro Asp Phe Asp Ser Lys Arg Ile Leu
545                 550                 555                 560 gac cct tcg cca aac gat cga ccc agc cgc ggc gcg tcg cgc tcc gcc     1728
Asp Pro Ser Pro Asn Asp Arg Pro Ser Arg Gly Ala Ser Arg Ser Ala
                565                 570                 575 tcg ggc acc aac ctt gcg cag acc att ttc aac acc atg aac acg gcc     1776
Ser Gly Thr Asn Leu Ala Gln Thr Ile Phe Asn Thr Met Asn Thr Ala
            580                 585                 590
```

| | | |
|---|---|---|
| aca cag ccg cta aac caa tgg ctc ggt atg gat ggg cgc ttc gag tgg<br>Thr Gln Pro Leu Asn Gln Trp Leu Gly Met Asp Gly Arg Phe Glu Trp<br>595                          600                        605 | | 1824 |
| gag cgt gtg gac gac tcg gat gcg gac gac gtg ttc ttt ttc ctc aac<br>Glu Arg Val Asp Asp Ser Asp Ala Asp Asp Val Phe Phe Phe Leu Asn<br>610                          615                        620 | | 1872 |
| cct gca gga gcc atc caa ggg cga tcg agg acg tct tct tgg ggt gct<br>Pro Ala Gly Ala Ile Gln Gly Arg Ser Arg Thr Ser Ser Trp Gly Ala<br>625                       630                        635                    640 | | 1920 |
| gga gca tgg acg cct tcg tct gct ggc gat ggt tct cgg tct cgg tca<br>Gly Ala Trp Thr Pro Ser Ser Ala Gly Asp Gly Ser Arg Ser Arg Ser<br>                     645                        650                        655 | | 1968 |
| agg agt cgc agt cgg acg agc tcg ttt gcg tca ggg cag att cag ctg<br>Arg Ser Arg Ser Arg Thr Ser Ser Phe Ala Ser Gly Gln Ile Gln Leu<br>660                          665                        670 | | 2016 |
| ggc gaa ggg ttc aag ctg gag gca ttg aca gag ctg cca aag gat aag<br>Gly Glu Gly Phe Lys Leu Glu Ala Leu Thr Glu Leu Pro Lys Asp Lys<br>              675                        680                        685 | | 2064 |
| cct ttt ggc gag gtg aca cga cga ctc agc ttg agt cgc aag cag aag<br>Pro Phe Gly Glu Val Thr Arg Arg Leu Ser Leu Ser Arg Lys Gln Lys<br>690                          695                        700 | | 2112 |
| cat gga ctg gtg ggc gac atg acc aag gat ccc gag gag att gag aag<br>His Gly Leu Val Gly Asp Met Thr Lys Asp Pro Glu Glu Ile Glu Lys<br>705                          710                        715                    720 | | 2160 |
| cag ggc gga ttt atg cat gag gga cac ttt gtc agc aca ccg ccc atc<br>Gln Gly Gly Phe Met His Glu Gly His Phe Val Ser Thr Pro Pro Ile<br>                          725                        730                        735 | | 2208 |
| acg gtt cag aac atg gat gat cct atg gat gca gtc aag tct aag gag<br>Thr Val Gln Asn Met Asp Asp Pro Met Asp Ala Val Lys Ser Lys Glu<br>740                          745                        750 | | 2256 |
| gca taa<br>Ala | | 2262 |

<210> SEQ ID NO 4
<211> LENGTH: 3280
<212> TYPE: DNA
<213> ORGANISM: Mortierella alpina

<400> SEQUENCE: 4

| | |
|---|---|
| atgggtctcc agatctatga cttcgtctca ttcttcttca ccctcctgct cgacatcttc | 60 |
| ttcagggaaa tccgtcctcg gggggcccac aagatccccc gacaaggacc cgtcattttt | 120 |
| gtcgccgccc ctcatgccaa tcaggtaggc cattgtcttt aatttggaag cttaaagtca | 180 |
| ccactttatg cgcaagagcc tcatggtccg taaggtacta atcgctgctt gcatgaaact | 240 |
| agtttgttga tccactcgtg ttgatgcgcg aatgtggccg acgagtctcg ttcctggctg | 300 |
| ccaaaaagtc aatggaccgt cgctggatag cgccatggc gcgttccatg aatgccagta | 360 |
| agtacaaaaa aaaaaaaaaa aaaaaaaaaa aacgacctat tcggcgtgag agtggcaacg | 420 |
| aaggggagag agatacacaa acgggccttt tgagtgcgtg tgtgcgtggg aaaagaatac | 480 |
| gagaacattc tcttgccagc aaaacgcgct tcctttctct tttctccgac gttgttgatg | 540 |
| gcgcctttg tatacacttc ctatccatcg tccctatccg agagatcaag gttttctgcg | 600 |
| tcgtgttatt ttaggccact ccgccgagat aacagacacg agctactgac cgattcaacg | 660 |
| agggttcaca caccgtccac aaccacctga gaaatgtgca ggccatgacg agtgtcgtgt | 720 |
| gccgtttctt ctttgatacc ataccgctcc tgcagtcatg ggccatcgt tatgccctga | 780 |
| cctcagcatt ggaatctgac gttttttct gctcgctctc ttgtcatctg cgttagttcc | 840 |

```
tgtggagcgt cctcaggact tggctaaggc tggttcggga acgatcaaac tggtggatcg    900
ctatggcgac cctctccgca tcactgggct cggtaccaaa ttcacaaagg aactctttgt    960
cggcgaccag atttcgctcc caaaggacgt tggaacctcg gctgtggtcg agatcatctc   1020
ggacactgaa ctgattgtca agaaagagtt caaggagctc aaggcactgg agcttttaac   1080
cagtgctgag ggatccaagt acaagtgcat gcctcacatg gaccagagca aggtctacaa   1140
gactgttttt gaacgcttaa atgctggcca ttgtgttggc atctttcctg aaggaggttc   1200
acacgatcgt gcagagatgc tgcccctgaa aggtaagcgc ccctcgtgag catcccaaca   1260
taacgggaat taccccacac ttgccttgtc cttgcgcatc tctgtatgaa cgtacactga   1320
ttgcattgca tatctccgtt tggattggat agctggtgtc accatcatgg cgcttggcgc   1380
actggccgct aaccctgacc tggaccttaa aattgtgacc tgcggcctga actatttcca   1440
cccccatcga ttccgttctc gcgccgttgt tgagtttggt gagcctttga ccgtgcctcc   1500
agaacttgtc gagatgtaca agaggggtgg agctgagaag cgcgaggcct gcggaaagct   1560
cctcgacacc atctacgatg cactcaagaa tgtcacactg aacgccccccg attacgaaac   1620 actcatggtg aggattggcg tgttttttgc atgcggctta tgtcatttgg agcaattgag   1680
accaacgtta acttaaaggg ctttaatatg gctggactgg atgtaggtta ttcaagctgc   1740
ccgccgtctc tacaagccaa cacatcgcaa gctgcagatc tctcaagttg tggagttgaa   1800
ccgtcgcttc gtcgctggtt atctgcactt tcaggacaac ccaaaggtga ttgatacaaa   1860
ggacaaagtt atgcactaca acactcagct acgctatcat ggacttcgcg accaccaggt   1920
caacatccgc acaactcggc gacatgccat tgaactattg atttggcgag ttgtgcagat   1980 ggtcttttttg agtctactag cgcttccagg gtaagaacga atgcagcagt ggtgtcatgt   2040
cacagacttt tgtgtgggcg gttagattga ggctagcact acttcacgcg attggatatt   2100
agactaacgc tttctctact tttagtacca tgatgaatct tccagttgcc atcgttgctc   2160
gcatcatcag caacaagaag gccaagggta tgtaatcgtc gcaatgacag cgacaaatct   2220
tttgattatc gggagaatgg cgtcagagga aaaaggccaa ggctaacgct ataatcattt   2280
tcacaattta acagagggctt tggctgcatc gaccgtgaaa attgcaggaa gggacgttct   2340
agccacatgg aagttgcttg tggccctggg attgatgccc gtcctttact tttcgtactc   2400
gtttgttatc ttttttgctgt gtggacggtt cgacattacg ctcaagaccc gcctcctgat   2460
cgcttgggcg gcttgggcct gcattccgtt tgtgacctac gccagtatcc gtttcggtga   2520
ggtgggtatc gatatcttca agtcgatccg tcctctcttc ttgtcaatca ttcccggcga   2580
ggaaaacacg atcaatgagc tccgcaagtc gcgtgcagag cttcaaaaga ccatcaacga   2640
gctcatcaat gagctggcgc cggaaatata ccccgacttt gattccaaac gaatcttgga   2700
cccttcgcca aacgatcgac ccagccgcgg cgcgtcgcgc tccgcctcgg caccaacct   2760 tgcgcagacc attttcaaca ccatgaacac ggccacacag ccgctaaacc aatggctcgg   2820
tatggatggg cgcttcgagt gggagcgtgt ggacgactcg gatgcggacg acgtgttctt   2880
tttcctcaac cctgcaggag ccatccaagg gcgatcgagg acgtcttctt ggggtgctgg   2940
agcatggacg ccttcgtctg ctggcgatgg ttctcggtct cggtcaagga gtcgcagtcg   3000
gacgagctcg tttgcgtcag ggcagattca gctgggcgaa gggttcaagc tggaggcatt   3060
gacagagctg ccaaaggata agcctttggg cgaggtgaca cgacgactca gcttgagtcg   3120
caagcagaag catggactgg tgggcgacat gaccaaggat cccgaggaga ttgagaagca   3180
```

| | |
|---|---|
| gggcggattt atgcatgagg acactttgt cagcacaccg cccatcacgg ttcagaacat | 3240 |
| ggatgatcct atggatgcag tcaagtctaa ggaggcataa | 3280 |

<210> SEQ ID NO 5
<211> LENGTH: 3087
<212> TYPE: DNA
<213> ORGANISM: Mortierella alpina

<400> SEQUENCE: 5

| | |
|---|---|
| atggcccttc agatctacga cttcgtgtcg ttcttcttca ctatcctgct cgacatcttc | 60 |
| ttcagggaga ttcgtcccag aggcgcacac aaaattccac aaaaaggacc cgtgatcttt | 120 |
| gttgccgctc ctcatgccaa tcaggtacgt gcacatgagg gctcgctttt ctcggagcgg | 180 |
| gcttcgtcca aaaagctgca caggctgaaa tgagagcgca tattcacctg gacacgggca | 240 |
| cagagttcat gcatgataag ccggatagca ggagccgaca ctgcagaaga gaccctctgg | 300 |
| accaacaaag aaaacatca tgacggaact agccttctcc ggaagagcca atggacgtca | 360 |
| ttggtagacg caaccgttcc aactaaccgg cgctcttgtc ctcatagttt gtcgatcctc | 420 |
| tcgtcttgat gcgtgagtgt ggccgtagag tctcattcct tgcggccaaa aagtctatgg | 480 |
| accgccggtg gattggtgct atggcacgct cgatgaatgc gagtaagttg cttggacttt | 540 |
| gacacgaaac tgttgccacg tcaagaatat cccacccctc ccgactcgac cacctccagc | 600 |
| tctcacctac acacacaaaa caggaaattt cagtgttctt caaggctttg gtggtgcttc | 660 |
| gaatggcgct acaaaaggcc tgctctaggg tgatagagtg ttggctttga tccttccgac | 720 |
| attctcggct cccttaccaa gacatttgtc ctgaatgctg attgatccga cactgctgaa | 780 |
| ccattcctac tcatagttcc tgttgaacgc ccgcaggatc ttgctaaagc gggttcggga | 840 |
| gtcatcaaac ttttggatcg ctatggtgat cctcttcgag tgacaggtgt cggcactaaa | 900 |
| ttcacaaagg agctacttgt gggagatcag atatctctcc caaggacgt tggctcctca | 960 |
| gccgtggtcg agatcatatc tgataccgag ctgattgtca agaaggaatt caaggagctc | 1020 |
| aaggccctcg aattattgac cagccctgat ggaaccaagt ataaatgcct acctcacatg | 1080 |
| gaccagacga atgtatacaa aactgtcttt gagcgcctca cgctggaca ttgcgttggc | 1140 |
| attttccccg aaggtggatc ccacgatcgc gctgagatgc tgccattgaa aggtacgtgt | 1200 |
| gctcgtgctt ctgcacagag cagagtagtt gatatggaac agaagaaaaa agacacgcga | 1260 |
| ccagctttga ttaacagcca cgtgtttcct ttacctttgc gaaacattat agctggagtc | 1320 |
| accatcatgg ctctgggcgc gttggccgcc aaccccttcgt tggacctcaa gattgtcacc | 1380 |
| tgcggcctca actactttca tcctcatcgc ttccgctcgc gtgcagtggt cgagtttggc | 1440 |
| gagccactga cggtccctcc tgagctggtc gaaatgtaca agcgaggcgg ggctgagaag | 1500 |
| cgtgaagcgt gcggaaagtt gctggataca atctatgagg ctcttcgcgg tgtcactctc | 1560 |
| aatgcacctg attacgaaac gttgatggta tggagcaaag gaccatagcg tggatgaagg | 1620 |
| aggacgtgga aaggacaagc accgctcaca gatttctcac tcttgtattt gtgattatct | 1680 |
| ctaggtcatt caagcggccc gtcgccttta caagcccact catcgcaagc tgcagatctc | 1740 |
| acaagtcgtg gagttgaacc gcaggttcgt cgcaggatac atgcacttca aggacaaccc | 1800 |
| taaagtcatt gaagccaagg acaaggtcat gcattacaac actcaacttc gataccatgg | 1860 |
| actgcgcgat catcaggtga acattcgcac aaccaggaaa cacgctatcg gcatgctcat | 1920 |
| ctcacggctc attcagatga tcttttttgag ttgtctggct ctacctgggt aagcacagct | 1980 |

-continued

```
tgaatctcga ccaggtcccg caatgatccc attgcggaga agtcactgac gcttgctctt      2040
cccgtgcttt tttgaataga accctgatga atcttccggt cgctattgtc gctcgtgtca      2100
tcagcaacaa gaaggccaaa ggtacgcctt gcggtttgtt atcttttcgt gtttgctttt      2160
gtgctcgcca ctggaaacta atatttctac atcactctgc aactggtaga ggcgctggct      2220
gcctcgacag tcaagattgc tggaagggat gtcctggcta catggaagct gctggtcgct      2280
ctaggattga tgcctgtcct ctacttcaca tattccgtca tggtctttat ctattgtggc      2340
cgcttcgaca tatcgttcaa gtcgcgtctc ttgatcgctt gggcagcatg ggcgctaatt      2400
cctttcgtaa cgtatgcaag catacgcttc ggtgaagttg gtatcgatat tttcaaatct      2460
atccgcccat tgttcttgtc catcatccca ggtgaagaga gcacgatcaa cgacttgcgc      2520
aaagcccgag cggaactcca aagactatc accaatctta tcaatgagct ggcgccgcag      2580
atttatcccg actttgattc gaagcgcatc ctcgatccgt ctcctgcaga tcgcccagc       2640 cgctcggcat caggtaccaa ccttgcacag acaatcttca acacggccgc tcagcctttg      2700
aaccaatggc taggcaagga cggccgcttt gaatgggagc gcaccgagga ttcggatgca      2760
gatgatgtgt tcttcttttt ggacccagca agaggaattc ttggacggtc gagggcgtcg      2820
tcctggggag gaggggcatt tacacctgcc gccgatgggt cgcgatcccg gaatcggagc      2880
aggacaagca gcttcacgtc gggacagatc cagcttggcg agggcttcaa actcgaggca      2940
ttgacggaac tgccgaggga caagcctttt gcagaggtga cgaggcggct gagtgtgagc      3000
cgcatgcaga gatacgggtt ggagggtatg acgcgctcgg acacggacga aaacgaaggc      3060
tctacagcca agtcaaaaga tatctag                                          3087
```

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 6
gaattcatgg gtctccagat ctatgacttc gtctc                                  35

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 7
gtcgacttat gcctccttag acttgactgc atcc                                   34

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 8
tctagaatgc ctgcaccaaa actcac                                            26

```
<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tctagaccac aaggtgatca ggaaga                                          26

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtgtaggaa gcccggaatt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcgtagatcc aacagactac                                                 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttgcctcttc caagagcaca                                                 20

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtcaagaagg aattcaagga gctcaag                                         27

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctgggatga tggacaagaa caatg                                           25
```

```
<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttttgaacgc ttaaatgctg gc                                           22

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtcttttga agctctgcac gcgac                                        25

<210> SEQ ID NO 17
<211> LENGTH: 717
<212> TYPE: PRT
<213> ORGANISM: Mortierella alpina

<400> SEQUENCE: 17

Met Ala Leu Gln Ile Tyr Asp Phe Val Ser Phe Phe Thr Ile Leu
 1               5                  10                  15

Leu Asp Ile Phe Phe Arg Glu Ile Arg Pro Arg Gly Ala His Lys Ile
                20                  25                  30

Pro Gln Lys Gly Pro Val Ile Phe Val Ala Ala Pro His Ala Asn Gln
            35                  40                  45

Phe Val Asp Pro Leu Val Leu Met Arg Glu Cys Gly Arg Arg Val Ser
        50                  55                  60

Phe Leu Ala Ala Lys Lys Ser Met Asp Arg Arg Trp Ile Gly Ala Met
65                  70                  75                  80

Ala Arg Ser Met Asn Ala Ile Pro Val Glu Arg Pro Gln Asp Leu Ala
                85                  90                  95

Lys Ala Gly Ser Gly Val Ile Lys Leu Leu Asp Arg Tyr Gly Asp Pro
            100                 105                 110

Leu Arg Val Thr Gly Val Gly Thr Lys Phe Thr Lys Glu Leu Leu Val
        115                 120                 125

Gly Asp Gln Ile Ser Leu Pro Lys Asp Val Gly Ser Ser Ala Val Val
    130                 135                 140

Glu Ile Ile Ser Asp Thr Glu Leu Ile Val Lys Lys Glu Phe Lys Glu
145                 150                 155                 160

Leu Lys Ala Leu Glu Leu Leu Thr Ser Pro Asp Gly Thr Lys Tyr Lys
                165                 170                 175

Cys Leu Pro His Met Asp Gln Thr Asn Val Tyr Lys Thr Val Phe Glu
            180                 185                 190

Arg Leu Asn Ala Gly His Cys Val Gly Ile Phe Pro Glu Gly Gly Ser
        195                 200                 205

His Asp Arg Ala Glu Met Leu Pro Leu Lys Ala Gly Val Thr Ile Met
    210                 215                 220

Ala Leu Gly Ala Leu Ala Ala Asn Pro Ser Leu Asp Leu Lys Ile Val
225                 230                 235                 240
```

-continued

```
Thr Cys Gly Leu Asn Tyr Phe His Pro His Arg Phe Arg Ser Arg Ala
                245                 250                 255

Val Val Glu Phe Gly Glu Pro Leu Thr Val Pro Pro Glu Leu Val Glu
            260                 265                 270

Met Tyr Lys Arg Gly Ala Glu Lys Arg Glu Ala Cys Gly Lys Leu
        275                 280                 285

Leu Asp Thr Ile Tyr Glu Ala Leu Arg Gly Val Thr Leu Asn Ala Pro
    290                 295                 300

Asp Tyr Glu Thr Leu Met Val Ile Gln Ala Arg Arg Leu Tyr Lys
305                 310                 315                 320

Pro Thr His Arg Lys Leu Gln Ile Ser Gln Val Val Glu Leu Asn Arg
                325                 330                 335

Arg Phe Val Ala Gly Tyr Met His Phe Lys Asp Asn Pro Lys Val Ile
            340                 345                 350

Glu Ala Lys Asp Lys Val Met His Tyr Asn Thr Gln Leu Arg Tyr His
        355                 360                 365

Gly Leu Arg Asp His Gln Val Asn Ile Arg Thr Arg Lys His Ala
    370                 375                 380

Ile Gly Met Leu Ile Ser Arg Leu Ile Gln Met Ile Phe Leu Ser Cys
385                 390                 395                 400

Leu Ala Leu Pro Gly Thr Leu Met Asn Leu Pro Val Ala Ile Val Ala
                405                 410                 415

Arg Val Ile Ser Asn Lys Lys Ala Lys Glu Ala Leu Ala Ala Ser Thr
            420                 425                 430

Val Lys Ile Ala Gly Arg Asp Val Leu Ala Thr Trp Lys Leu Leu Val
        435                 440                 445

Ala Leu Gly Leu Met Pro Val Leu Tyr Phe Thr Tyr Ser Val Met Val
    450                 455                 460

Phe Ile Tyr Cys Gly Arg Phe Asp Ile Ser Phe Lys Ser Arg Leu Leu
465                 470                 475                 480

Ile Ala Trp Ala Ala Trp Ala Leu Ile Pro Phe Val Thr Tyr Ala Ser
                485                 490                 495

Ile Arg Phe Gly Glu Val Gly Ile Asp Ile Phe Lys Ser Ile Arg Pro
            500                 505                 510

Leu Phe Leu Ser Ile Ile Pro Gly Glu Glu Ser Thr Ile Asn Asp Leu
        515                 520                 525

Arg Lys Ala Arg Ala Glu Leu Gln Lys Thr Ile Thr Asn Leu Ile Asn
    530                 535                 540

Glu Leu Ala Pro Gln Ile Tyr Pro Asp Phe Asp Ser Lys Arg Ile Leu
545                 550                 555                 560

Asp Pro Ser Pro Ala Asp Arg Pro Ser Arg Ser Ala Ser Gly Thr Asn
                565                 570                 575

Leu Ala Gln Thr Ile Phe Asn Thr Ala Ala Gln Pro Leu Asn Gln Trp
            580                 585                 590

Leu Gly Lys Asp Gly Arg Phe Glu Trp Glu Arg Thr Glu Asp Ser Asp
        595                 600                 605

Ala Asp Asp Val Phe Phe Leu Asp Pro Ala Arg Gly Ile Leu Gly
    610                 615                 620

Arg Ser Arg Ala Ser Ser Trp Gly Gly Gly Ala Phe Thr Pro Ala Ala
625                 630                 635                 640

Asp Gly Ser Arg Ser Arg Asn Arg Ser Arg Thr Ser Ser Phe Thr Ser
                645                 650                 655
```

-continued

```
Gly Gln Ile Gln Leu Gly Glu Gly Phe Lys Leu Glu Ala Leu Thr Glu
            660                 665                 670

Leu Pro Arg Asp Lys Pro Phe Ala Glu Val Thr Arg Arg Leu Ser Val
        675                 680                 685

Ser Arg Met Gln Arg Tyr Gly Leu Glu Gly Met Thr Arg Ser Asp Thr
    690                 695                 700

Asp Glu Asn Glu Gly Ser Thr Ala Lys Ser Lys Asp Ile
705                 710                 715

<210> SEQ ID NO 18
<211> LENGTH: 716
<212> TYPE: PRT
<213> ORGANISM: Mortierella alpina
<220> FEATURE:
<221> NAME/KEY: MOD_RES
<222> LOCATION: (141)..(141)
<223> OTHER INFORMATION: Any amino acid

<400> SEQUENCE: 18

Met Ala Leu Gln Ile Tyr Asp Phe Val Ser Phe Phe Thr Ile Leu
1               5                   10                  15

Leu Asp Ile Phe Phe Arg Glu Ile Arg Pro Arg Gly Ala His Lys Ile
            20                  25                  30

Pro Gln Lys Gly Pro Val Ile Phe Val Ala Ala Pro His Ala Asn Gln
        35                  40                  45

Phe Val Asp Pro Leu Val Leu Met Arg Glu Cys Gly Arg Arg Val Ser
    50                  55                  60

Phe Leu Ala Ala Lys Lys Ser Met Asp Arg Arg Trp Ile Gly Ala Met
65                  70                  75                  80

Ala Arg Ser Met Asn Ala Ile Pro Val Glu Arg Pro Gln Asp Leu Ala
                85                  90                  95

Lys Ala Gly Ser Gly Ile Ile Lys Leu Leu Asp Arg Tyr Gly Asp Pro
            100                 105                 110

Leu Arg Val Thr Gly Val Gly Thr Lys Phe Thr Lys Glu Leu Leu Val
        115                 120                 125

Gly Asp Gln Ile Ser Leu Pro Lys Asp Val Gly Val Xaa Ala Val Gly
    130                 135                 140

Glu Ile Ile Ser Asp Thr Glu Leu Ile Val Lys Lys Glu Phe Lys Glu
145                 150                 155                 160

Leu Lys Ala Leu Glu Leu Leu Thr Ser Ala Gly Thr Lys Tyr Lys
                165                 170                 175

Cys Leu Pro His Met Asp Gln Thr Asn Val Tyr Lys Thr Val Phe Glu
            180                 185                 190

Arg Leu Asn Ala Gly His Cys Val Gly Ile Phe Pro Glu Gly Gly Ser
        195                 200                 205

His Asp Arg Ala Glu Met Leu Pro Leu Lys Ala Gly Val Thr Ile Met
    210                 215                 220

Ala Leu Gly Ala Leu Ala Ala Asn Pro Ser Leu Asp Leu Lys Ile Val
225                 230                 235                 240

Thr Cys Gly Leu Asn Tyr Phe His Pro His Arg Phe Arg Ser Arg Ala
                245                 250                 255

Val Val Glu Phe Gly Glu Pro Leu Thr Val Ser Pro Glu Leu Val Glu
            260                 265                 270

Met Tyr Lys Arg Gly Gly Ala Glu Lys Arg Glu Ala Cys Gly Lys Leu
        275                 280                 285
```

```
Leu Asp Thr Ile Tyr Glu Ala Leu Arg Gly Val Thr Leu Asn Ala Pro
        290                 295                 300

Asp Tyr Glu Thr Leu Met Val Ile Gln Ala Ala Arg Arg Leu Tyr Lys
305                 310                 315                 320

Pro Thr His Arg Lys Leu Gln Ile Ser Gln Val Val Glu Leu Asn Arg
                325                 330                 335

Arg Phe Val Ala Gly Tyr Met His Phe Lys Asp Asn Pro Lys Val Ile
                340                 345                 350

Glu Ala Lys Asp Lys Val Met His Tyr Asn Thr Gln Leu Arg Tyr His
                355                 360                 365

Gly Leu Arg Asp His Gln Val Asn Ile Arg Thr Thr Arg Lys His Ala
370                 375                 380

Ile Gly Met Leu Ile Ser Arg Leu Ile Gln Met Ile Phe Leu Ser Cys
385                 390                 395                 400

Leu Ala Leu Pro Gly Thr Leu Met Asn Leu Pro Val Ala Ile Val Ala
                405                 410                 415

Arg Val Ile Ser Asn Lys Lys Ala Lys Glu Ala Leu Ala Ala Ser Thr
                420                 425                 430

Val Lys Ile Ala Gly Arg Asp Val Leu Ala Thr Trp Lys Leu Leu Val
                435                 440                 445

Ala Leu Gly Leu Met Pro Val Leu Tyr Phe Thr Tyr Ser Val Met Val
                450                 455                 460

Phe Ile Tyr Cys Ser Arg Phe Asp Leu Ser Phe Lys Ser Arg Leu Leu
465                 470                 475                 480

Val Ala Trp Ala Ala Trp Ala Leu Ile Pro Phe Val Thr Tyr Ala Ser
                485                 490                 495

Ile Arg Phe Gly Glu Val Gly Ile Asp Ile Phe Lys Ser Ile Arg Pro
                500                 505                 510

Leu Phe Leu Ser Ile Ile Pro Gly Glu Ser Thr Ile Asn Asp Leu
                515                 520                 525

Arg Lys Ala Arg Ala Glu Leu Gln Lys Thr Ile Thr Asn Leu Ile Asn
530                 535                 540

Glu Leu Ala Pro Gln Ile Tyr Pro Asp Phe Asp Ser Lys Arg Ile Leu
545                 550                 555                 560

Asp Pro Ser Pro Ala Asp Arg Pro Ser Arg Ser Ala Ser Gly Thr Asn
                565                 570                 575

Leu Ala Gln Thr Ile Phe Asn Thr Ala Ala Gln Pro Leu Asn Gln Trp
                580                 585                 590

Leu Gly Lys Asp Gly Arg Phe Glu Trp Glu Arg Thr Glu Asp Ser Asp
                595                 600                 605

Ala Asp Asp Val Phe Phe Phe Leu Asp Pro Ala Arg Gly Ile Met Gly
                610                 615                 620

Arg Ser Arg Ala Ser Ser Trp Gly Gly Gly Ala Phe Thr Pro Ala Val
625                 630                 635                 640

Asp Gly Ser Arg Ser Arg Asn Arg Ser Arg Thr Ser Ser Phe Thr Ser
                645                 650                 655

Gly Gln Ile Gln Leu Gly Glu Gly Phe Lys Leu Glu Ala Leu Thr Glu
                660                 665                 670

Leu Pro Arg Asp Asn Pro Phe Ala Glu Val Thr Arg Arg Leu Ser Val
                675                 680                 685
```

Ser Arg Met Gln Arg Tyr Gly Leu Glu Gly Met Thr Arg Ser Asp Thr
690                 695                 700

Asp Glu Asn Glu Gly Pro Ala Lys Ser Lys Asp Ile
705                 710                 715

<210> SEQ ID NO 19
<211> LENGTH: 759
<212> TYPE: PRT
<213> ORGANISM: Saccharomyces cerevisiae

<400> SEQUENCE: 19

Met Pro Ala Pro Lys Leu Thr Glu Lys Phe Ala Ser Ser Lys Ser Thr
1               5                   10                  15

Gln Lys Thr Thr Asn Tyr Ser Ser Ile Glu Ala Lys Ser Val Lys Thr
            20                  25                  30

Ser Ala Asp Gln Ala Tyr Ile Tyr Gln Glu Pro Ser Ala Thr Lys Lys
        35                  40                  45

Ile Leu Tyr Ser Ile Ala Thr Trp Leu Leu Tyr Asn Ile Phe His Cys
50                  55                  60

Phe Phe Arg Glu Ile Arg Gly Arg Gly Ser Phe Lys Val Pro Gln Gln
65                  70                  75                  80

Gly Pro Val Ile Phe Val Ala Ala Pro His Ala Asn Gln Phe Val Asp
                85                  90                  95

Pro Val Ile Leu Met Gly Glu Val Lys Lys Ser Val Asn Arg Arg Val
            100                 105                 110

Ser Phe Leu Ile Ala Glu Ser Ser Leu Lys Gln Pro Pro Ile Gly Phe
        115                 120                 125

Leu Ala Ser Phe Phe Met Ala Ile Gly Val Val Arg Pro Gln Asp Asn
130                 135                 140

Leu Lys Pro Ala Glu Gly Thr Ile Arg Val Asp Pro Thr Asp Tyr Lys
145                 150                 155                 160

Arg Val Ile Gly His Asp Thr His Phe Leu Thr Asp Cys Met Pro Lys
                165                 170                 175

Gly Leu Ile Gly Leu Pro Lys Ser Met Gly Phe Gly Glu Ile Gln Ser
            180                 185                 190

Ile Glu Ser Asp Thr Ser Leu Thr Leu Arg Lys Glu Phe Lys Met Ala
        195                 200                 205

Lys Pro Glu Ile Lys Thr Ala Leu Leu Thr Gly Thr Thr Tyr Lys Tyr
210                 215                 220

Ala Ala Lys Val Asp Gln Ser Cys Val Tyr His Arg Val Phe Glu His
225                 230                 235                 240

Leu Ala His Asn Asn Cys Ile Gly Ile Phe Pro Glu Gly Gly Ser His
                245                 250                 255

Asp Arg Thr Asn Leu Leu Pro Leu Lys Ala Gly Val Ala Ile Met Ala
            260                 265                 270

Leu Gly Cys Met Asp Lys His Pro Asp Val Asn Val Lys Ile Val Pro
        275                 280                 285

Cys Gly Met Asn Tyr Phe His Pro His Lys Phe Arg Ser Arg Ala Val
290                 295                 300

Val Glu Phe Gly Asp Pro Ile Glu Ile Pro Lys Glu Leu Val Ala Lys
305                 310                 315                 320

Tyr His Asn Pro Glu Thr Asn Arg Asp Ala Val Lys Glu Leu Leu Asp
                325                 330                 335

Thr Ile Ser Lys Gly Leu Gln Ser Val Thr Val Thr Cys Ser Asp Tyr
            340                 345                 350

-continued

Glu Thr Leu Met Val Val Gln Thr Ile Arg Arg Leu Tyr Met Thr Gln
            355                 360                 365

Phe Ser Thr Lys Leu Pro Leu Pro Leu Ile Val Glu Met Asn Arg Arg
    370                 375                 380

Met Val Lys Gly Tyr Glu Phe Tyr Arg Asn Asp Pro Lys Ile Ala Asp
385                 390                 395                 400

Leu Thr Lys Asp Ile Met Ala Tyr Asn Ala Ala Leu Arg His Tyr Asn
                405                 410                 415

Leu Pro Asp His Leu Val Glu Glu Ala Lys Val Asn Phe Ala Lys Asn
            420                 425                 430

Leu Gly Leu Val Phe Phe Arg Ser Ile Gly Leu Cys Ile Leu Phe Ser
            435                 440                 445

Leu Ala Met Pro Gly Ile Ile Met Phe Ser Pro Val Phe Ile Leu Ala
    450                 455                 460

Lys Arg Ile Ser Gln Glu Lys Ala Arg Thr Ala Leu Ser Lys Ser Thr
465                 470                 475                 480

Val Lys Ile Lys Ala Asn Asp Val Ile Ala Thr Trp Lys Ile Leu Ile
                485                 490                 495

Gly Met Gly Phe Ala Pro Leu Leu Tyr Ile Phe Trp Ser Val Leu Ile
            500                 505                 510

Thr Tyr Tyr Leu Arg His Lys Pro Trp Asn Lys Ile Tyr Val Phe Ser
            515                 520                 525

Gly Ser Tyr Ile Ser Cys Val Ile Val Thr Tyr Ser Ala Leu Ile Val
    530                 535                 540

Gly Asp Ile Gly Met Asp Gly Phe Lys Ser Leu Arg Pro Leu Val Leu
545                 550                 555                 560

Ser Leu Thr Ser Pro Lys Gly Leu Gln Lys Leu Gln Lys Asp Arg Arg
                565                 570                 575

Asn Leu Ala Glu Arg Ile Ile Glu Val Val Asn Asn Phe Gly Ser Glu
            580                 585                 590

Leu Phe Pro Asp Phe Asp Ser Ala Ala Leu Arg Glu Glu Phe Asp Val
            595                 600                 605

Ile Asp Glu Glu Glu Asp Arg Lys Thr Ser Glu Leu Asn Arg Arg
    610                 615                 620

Lys Met Leu Arg Lys Gln Lys Ile Lys Arg Gln Glu Lys Asp Ser Ser
625                 630                 635                 640

Ser Pro Ile Ile Ser Gln Arg Asp Asn His Asp Ala Tyr Glu His His
                645                 650                 655

Asn Gln Asp Ser Asp Gly Val Ser Leu Val Asn Ser Asp Asn Ser Leu
            660                 665                 670

Ser Asn Ile Pro Leu Phe Ser Ser Thr Phe His Arg Lys Ser Glu Ser
            675                 680                 685

Ser Leu Ala Ser Thr Ser Val Ala Pro Ser Ser Ser Ser Glu Phe Glu
    690                 695                 700

Val Glu Asn Glu Ile Leu Glu Glu Lys Asn Gly Leu Ala Ser Lys Ile
705                 710                 715                 720

Ala Gln Ala Val Leu Asn Lys Arg Ile Gly Glu Asn Thr Ala Arg Glu
                725                 730                 735

Glu Glu Glu Glu Glu Glu Glu Glu Glu Glu Glu Glu Glu Glu Glu Glu
            740                 745                 750

Glu Gly Lys Glu Gly Asp Ala
            755

```
<210> SEQ ID NO 20
<211> LENGTH: 743
<212> TYPE: PRT
<213> ORGANISM: Saccharomyces cerevisiae

<400> SEQUENCE: 20

Met Ser Ala Pro Ala Ala Asp His Asn Ala Ala Lys Pro Ile Pro His
1               5                   10                  15

Val Pro Gln Ala Ser Arg Arg Tyr Lys Asn Ser Tyr Asn Gly Phe Val
            20                  25                  30

Tyr Asn Ile His Thr Trp Leu Tyr Asp Val Ser Val Phe Leu Phe Asn
        35                  40                  45

Ile Leu Phe Thr Ile Phe Phe Arg Glu Ile Lys Val Arg Gly Ala Tyr
    50                  55                  60

Asn Val Pro Glu Val Gly Val Pro Thr Ile Leu Val Cys Ala Pro His
65                  70                  75                  80

Ala Asn Gln Phe Ile Asp Pro Ala Leu Val Met Ser Gln Thr Arg Leu
                85                  90                  95

Leu Lys Thr Ser Ala Gly Lys Ser Arg Ser Arg Met Pro Cys Phe Val
            100                 105                 110

Thr Ala Glu Ser Ser Phe Lys Lys Arg Phe Ile Ser Phe Phe Gly His
        115                 120                 125

Ala Met Gly Gly Ile Pro Val Pro Arg Ile Gln Asp Asn Leu Lys Pro
    130                 135                 140

Val Asp Glu Asn Leu Glu Ile Tyr Ala Pro Asp Leu Lys Asn His Pro
145                 150                 155                 160

Glu Ile Ile Lys Gly Arg Ser Lys Asn Pro Gln Thr Thr Pro Val Asn
                165                 170                 175

Phe Thr Lys Arg Phe Ser Ala Lys Ser Leu Leu Gly Leu Pro Asp Tyr
            180                 185                 190

Leu Ser Asn Ala Gln Ile Lys Glu Ile Pro Asp Asp Glu Thr Ile Ile
        195                 200                 205

Leu Ser Ser Pro Phe Arg Thr Ser Lys Ser Lys Val Val Glu Leu Leu
    210                 215                 220

Thr Asn Gly Thr Asn Phe Lys Tyr Ala Glu Lys Ile Asp Asn Thr Glu
225                 230                 235                 240

Thr Phe Gln Ser Val Phe Asp His Leu His Thr Lys Gly Cys Val Gly
                245                 250                 255

Ile Phe Pro Glu Gly Gly Ser His Asp Arg Pro Ser Leu Leu Pro Ile
            260                 265                 270

Lys Ala Gly Val Ala Ile Met Ala Leu Gly Ala Val Ala Ala Asp Pro
        275                 280                 285

Thr Met Lys Val Ala Val Val Pro Cys Gly Leu His Tyr Phe His Arg
    290                 295                 300

Asn Lys Phe Arg Ser Arg Ala Val Leu Glu Tyr Gly Glu Pro Ile Val
305                 310                 315                 320

Val Asp Gly Lys Tyr Gly Glu Met Tyr Lys Asp Ser Pro Arg Glu Thr
                325                 330                 335

Val Ser Lys Leu Leu Lys Lys Ile Thr Asn Ser Leu Phe Ser Val Thr
            340                 345                 350

Glu Asn Ala Pro Asp Tyr Asp Thr Leu Met Val Ile Gln Ala Ala Arg
        355                 360                 365

Arg Leu Tyr Gln Pro Val Lys Val Arg Leu Pro Leu Pro Ala Ile Val
    370                 375                 380
```

```
Glu Ile Asn Arg Arg Leu Leu Phe Gly Tyr Ser Lys Phe Lys Asp Asp
385                 390                 395                 400

Pro Arg Ile Ile His Leu Lys Lys Leu Val Tyr Asp Tyr Asn Arg Lys
                405                 410                 415

Leu Asp Ser Val Gly Leu Lys Asp His Gln Val Met Gln Leu Lys Thr
            420                 425                 430

Thr Lys Leu Glu Ala Leu Arg Cys Phe Val Thr Leu Ile Val Arg Leu
        435                 440                 445

Ile Lys Phe Ser Val Phe Ala Ile Leu Ser Leu Pro Gly Ser Ile Leu
    450                 455                 460

Phe Thr Pro Ile Phe Ile Ile Cys Arg Val Tyr Ser Glu Lys Lys Ala
465                 470                 475                 480

Lys Glu Gly Leu Lys Lys Ser Leu Val Lys Ile Lys Gly Thr Asp Leu
            485                 490                 495

Leu Ala Thr Trp Lys Leu Ile Val Ala Leu Ile Leu Ala Pro Ile Leu
            500                 505                 510

Tyr Val Thr Tyr Ser Ile Leu Leu Ile Ile Leu Ala Arg Lys Gln His
            515                 520                 525

Tyr Cys Arg Ile Trp Val Pro Ser Asn Asn Ala Phe Ile Gln Phe Val
530                 535                 540

Tyr Phe Tyr Ala Leu Leu Val Phe Thr Thr Tyr Ser Ser Leu Lys Thr
545                 550                 555                 560

Gly Glu Ile Gly Val Asp Leu Phe Lys Ser Leu Arg Pro Leu Phe Val
                565                 570                 575

Ser Ile Val Tyr Pro Gly Lys Lys Ile Glu Glu Ile Gln Thr Thr Arg
            580                 585                 590

Lys Asn Leu Ser Leu Glu Leu Thr Ala Val Cys Asn Asp Leu Gly Pro
        595                 600                 605

Leu Val Phe Pro Asp Tyr Asp Lys Leu Ala Thr Glu Ile Phe Ser Lys
    610                 615                 620

Arg Asp Gly Tyr Asp Val Ser Ser Asp Ala Glu Ser Ser Ile Ser Arg
625                 630                 635                 640

Met Ser Val Gln Ser Arg Ser Arg Ser Ser Ile His Ser Ile Gly
                645                 650                 655

Ser Leu Ala Ser Asn Ala Leu Ser Arg Val Asn Ser Arg Gly Ser Leu
            660                 665                 670

Thr Asp Ile Pro Ile Phe Ser Asp Ala Lys Gln Gly Gln Trp Lys Ser
        675                 680                 685

Glu Gly Glu Thr Ser Glu Asp Glu Asp Glu Phe Asp Gly Lys Asn Pro
    690                 695                 700

Ala Ile Val Gln Thr Ala Arg Ser Ser Asp Leu Asn Lys Glu Asn Ser
705                 710                 715                 720

Arg Asn Thr Asn Ile Ser Ser Lys Ile Ala Ser Leu Val Arg Gln Lys
                725                 730                 735

Arg Glu His Glu Lys Lys Glu
                740
```